United States Patent
Shirai et al.

(10) Patent No.: US 7,718,754 B2
(45) Date of Patent: May 18, 2010

(54) PROMOTER FOR POLYCONDENSATION REACTION

(75) Inventors: Eiji Shirai, Wakayama (JP); Yoshitomo Kimura, Wakayama (JP); Yasunori Inagaki, Wakayama (JP); Takashi Kubo, Wakayama (JP); Naoki Morita, Wakayama (JP); Ryo Koike, Wakayama (JP); Hiromi Iida, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/167,565

(22) Filed: Jul. 3, 2008

(65) Prior Publication Data

US 2009/0036635 A1     Feb. 5, 2009

(30) Foreign Application Priority Data

| Jul. 30, 2007 | (JP) | 2007-197984 |
| Jul. 30, 2007 | (JP) | 2007-197985 |
| Jul. 30, 2007 | (JP) | 2007-197987 |
| Jul. 30, 2007 | (JP) | 2007-197988 |
| Mar. 11, 2008 | (JP) | 2008-061635 |

(51) Int. Cl.
  C08G 63/00 (2006.01)
  C08G 63/02 (2006.01)

(52) U.S. Cl. ............ 528/181; 435/156; 568/772; 528/190; 528/271; 528/272; 528/279

(58) Field of Classification Search .......... 435/156; 568/772; 528/181, 190, 271, 272, 279
See application file for complete search history.

(56) References Cited

U.S. PATENT DOCUMENTS

| 2,440,315 | A | * | 4/1948 | Tuve ............ 436/138 |
| 4,943,677 | A | * | 7/1990 | Rokicki .......... 528/405 |
| 6,326,115 | B1 | | 12/2001 | Nakanishi et al. |
| 7,491,346 | B2 | * | 2/2009 | Hikosaka ........ 252/501.1 |
| 2003/0158372 | A1 | | 8/2003 | Shirai et al. |
| 2004/0086797 | A1 | | 5/2004 | Kubo et al. |

FOREIGN PATENT DOCUMENTS

| JP | 08-020636 | 1/1996 |
| JP | 10-239903 | 9/1998 |
| JP | 11-133668 | 5/1999 |
| JP | 2003-186250 | 7/2003 |
| JP | 2003-201342 | 7/2003 |
| JP | 2004-151246 | 5/2004 |
| JP | 2006-091318 | 4/2006 |
| JP | 2006-350035 | 12/2006 |

* cited by examiner

Primary Examiner—Terressa M Boykin
(74) Attorney, Agent, or Firm—Oblon, Spivak, McClelland, Maier & Neustadt, L.L.P.

(57) ABSTRACT

A promoter for a polycondensation reaction used together with a catalyst in a polycondensation reaction, the promoter for a polycondensation reaction comprising a pyrogallol compound having a benzene ring of which three hydrogen atoms adjacent to each other are substituted by hydroxyl groups; and a polycondensation resin obtained by polycondensing raw material monomers using the promoter as defined above and the catalyst. A polycondensation resin can be produced using the promoter of the present invention together with a catalyst in a polycondensation reaction, and the polycondensation resin can be used in various applications including, for example, films, sheets, fibers, toner materials for electrophotography, and the like.

18 Claims, No Drawings

PROMOTER FOR POLYCONDENSATION REACTION

FIELD OF THE INVENTION

The present invention relates to a promoter for a polycondensation reaction used together with a catalyst in a polycondensation reaction, a polycondensation resin obtained using the promoter, which can be used in various applications including, for example, films, sheets, fibers, toner materials for electrophotography, and the like, and a method for producing the polycondensation resin.

BACKGROUND OF THE INVENTION

Polycondensation resins such as polyesters and polyamide have been used in various applications, such as films, sheets, and fibers, utilizing their chemical and physical properties, and various studies have been made on catalysts for accelerating a polycondensation reaction and promoters for enhancing the activity of the catalyst depending upon the applications of the resins obtained.

For example, as a catalyst used in the production of a polycondensation resin used in a resin binder for a toner, various tin compounds have been studied, taking into consideration not only catalytic activity but also influences to the properties of the toner such as triboelectric chargeability. In recent years, a tin(II) compound without containing a Sn—C bond is more likely to be used as a catalyst than a tin compound having a Sn—C bond, such as dibutyltin oxide, from the viewpoint of safety or the like (see JP-A-2003-186250, or the like).

On the other hand, reports have been made that a polycondensation reaction is accelerated by using a tin(II) compound without containing a Sn—C bond together with an amide compound or an amine compound, thereby shortening the reaction time, whereby a resin having a shorter heat history is obtained (see JP-A-2006-350035, and the like).

In addition, as a catalyst to be used as a substitute for a tin compound having a Sn—C bond such as dibutyltin oxide, a titanium compound is likely to be preferably used, from the viewpoint of safety, or the like (see JP-A-2003-201342 (corresponding to US-A-2003-158372), JP-A-2004-151246 (corresponding to US-A-2004-086797), JP-A-2006-91318, and the like).

SUMMARY OF THE INVENTION

The present invention relates to a promoter for a polycondensation reaction used together with a catalyst in a polycondensation reaction, the promoter for a polycondensation reaction containing a pyrogallol compound having a benzene ring of which three hydrogen atoms adjacent to each other are substituted by hydroxyl groups; and a polycondensation resin obtained by polycondensing raw material monomers using the promoter as defined above and the catalyst.

DETAILED DESCRIPTION OF THE INVENTION

The present invention relates to a promoter for a polycondensation reaction effective in enhancing activity of a catalytic and shortening the reaction time, a polycondensation resin obtained by using the promoter, and a method for producing the polycondensation resin.

In addition, the present invention relates to a method for producing a polycondensation resin capable of controlling the reaction rate of a polycondensation reaction, and having a narrow distribution of a softening point, and a polycondensation resin obtained by the method.

Since the promoter for a polycondensation reaction of the present invention is capable of enhancing an activity of the catalyst by the promoter used together with a catalyst, so that the reaction time can be shortened.

In addition, according to the method of the present invention, a polycondensation resin having a narrow molecular weight distribution (softening point distribution), while controlling the reaction rate as occasion demands, can be produced.

These and other advantages of the present invention will be apparent from the following description.

A first embodiment and a second embodiment of the present invention will be described hereinbelow. A promoter in the first embodiment means a pyrogallol compound having a benzene ring of which three hydrogen atoms adjacent to each other are substituted by hydroxyl groups, and a promoter in the second embodiment means a compound having a benzene ring of which at least two hydrogen atoms are substituted by hydroxyl groups.

First Embodiment

A first embodiment of the present invention is a promoter for a polycondensation reaction containing a pyrogallol compound having a benzene ring of which three hydrogen atoms adjacent to each other are substituted by hydroxyl groups. Although not wanted to be limited by theory, the reasons therefor are unclear, but assumed to be as follows. Since the pyrogallol compound is used as a promoter together with a catalyst in a polycondensation reaction, the lowering of the catalytic activity that accompanies the progress of the reaction is suppressed, so that a high catalytic activity is maintained, whereby the reaction time can be shortened. As a result, it is considered that a polycondensation resin having a short heat history is obtained, and an increase in a low-molecular weight component or a volatile organic component can also be prevented.

The above-mentioned pyrogallol compound includes pyrogallol, pyrogallic acid, pyrogallic acid esters, benzophenone derivatives such as 2,3,4-trihydroxybenzophenone and 2,2',3,4-tetrahydroxybenzophenone, catechin derivatives such as epigallocatechin and epigallocatechin gallate, and the like. Among them, a compound represented by the formula (I):

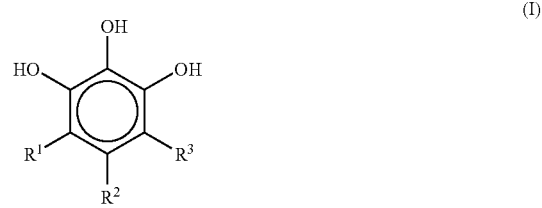

wherein each of $R^1$ to $R^3$ is independently a hydrogen atom or —$COOR^4$, wherein $R^4$ is a hydrogen atom or a hydrocarbon group having 1 to 12 carbon atoms, preferably an alkyl group or an alkenyl group, is preferable, from the viewpoint of transparency of the resin obtained. In the formula, the hydrocarbon group of $R^4$ has preferably from 1 to 8 carbon atoms, and more preferably from 1 to 4 carbon atoms, from the viewpoint of reaction activity. Among the compounds represented by the formula (I), a compound where each of $R^1$ and $R^3$ is a hydrogen atom, and $R^2$ is a hydrogen atom or —COOR$^4$ is more preferable. Specific examples include pyrogallol ($R^1$ to $R^3$: hydrogen atoms), pyrogallic acid ($R^1$ and $R^3$: hydrogen atoms, $R^2$: —COOH), pyrogallic acid esters, such as ethyl pyrogallate ($R^1$ and $R^3$: hydrogen atoms, $R^2$: —COOC$_2$H$_5$), propyl pyrogallate ($R^1$ and $R^3$: hydrogen atoms, $R^2$: —COOC$_3$H$_7$), butyl pyrogallate ($R^1$ and $R^3$: hydrogen atoms, $R^2$:—COOC$_4$H$_9$), octyl pyrogallate ($R^1$ and $R^3$: hydrogen atoms, $R^2$: —COOC$_8$H$_{17}$), and lauryl pyrogallate ($R^1$ and $R^3$: hydrogen atoms, $R^2$: —COOC$_{12}$H$_{25}$), and the like. Pyrogallic acid and the pyrogallic acid esters are preferred from the viewpoint of transparency of the resin.

The catalyst for a polycondensation reaction used together with the promoter of the present invention includes tin catalysts, titanium catalysts, metal compounds such as antimony trioxide, zinc acetate, germanium dioxide, and the like.

The tin catalyst includes a tin compound having a Sn—C bond such as dibutyltin oxide, and a tin(II) compound without containing a Sn—C bond. In a case where a tin(II) compound without containing a Sn—C bond is used, the effects of the promoter of the present invention are more remarkably exhibited.

Although a tin(II) without containing a Sn—C bond, such as a tin(II) compound having a Sn—O bond is more excellent in the aspect of safety than a tin compound having a Sn—C bond, the catalytic activity is worse than the tin compound having a Sn—C bond, so that a long reaction time or a high reaction temperature is necessitated. Therefore, there are some disadvantages of not only an increase in the production costs, but also an increase in a low-molecular weight component or an increase in a volatile organic component. Although not wanting to be limited by theory, the reasons therefor are presumably as follows. The tin(II) compound without containing a Sn—C bond is an unstable compound as compared to the tin(II) compound having a Sn—C bond, because the catalytic activity is more likely to be lost by undergoing structural changes. However, although the reasons therefor are unclear, by the coexistence of the above-mentioned pyrogallol compound, the lowering of the catalytic activity of the tin(II) compound without containing a Sn—C bond is suppressed, maintaining a high catalytic activity, whereby the reaction time can be shortened. Consequently, a polycondensation resin having a short heat history is obtained, and an increase in a low-molecular weight component or a volatile organic component due to monomer decomposition during the reaction with the shortening of the reaction time can also be prevented. The polycondensation resin of the present invention obtained by using the above-mentioned pyrogallol compound together can maintain excellent fluidity of the toner even when the polycondensation resin is used as a resin binder for a toner.

As the tin(II) compound without containing a Sn—C bond, a tin(II) compound having a Sn—O bond, a tin(II) compound having a Sn—X bond, wherein X is a halogen atom, or the like is preferable, and the tin(II) compound having a Sn—O bond is more preferable.

The tin(II) compound having a Sn—O bond includes tin (II) carboxylates having a carboxylate group having 2 to 28 carbon atoms, such as tin(II) oxalate, tin(II) acetate, tin(II) octanoate, tin(II) 2-ethylhexanoate, tin(II) laurate, tin(II) stearate, and tin(II) oleate; alkoxy tin(II) compound having an alkoxy group having 2 to 28 carbon atoms, such as octyloxy tin(II), lauroxy tin(II), stearoxy tin(II), and oleyloxy tin(II); tin(II) oxide; tin(II) sulfate; and the like. The tin(II) having a Sn—X bond, wherein X is a halogen atom, includes tin(II) halides, such as tin(II) chloride and tin(II) bromide, and the like. Among them, a fatty acid tin(II) represented by $(R^5COO)_2Sn$, wherein $R^5$ is an alkyl group or an alkenyl group having 5 to 19 carbon atoms, an alkoxy tin(II) represented by $(R^6O)_2Sn$, wherein $R^6$ is an alkyl group or alkenyl group having 6 to 20 carbon atoms, and tin(II) oxide represented by SnO are preferable; the fatty acid tin(II) represented by $(R^5COO)_2Sn$ and tin oxide (II) are more preferable; tin(II) octanoate, tin(II) 2-ethylhexanoate, tin(II) stearate, and tin (II) oxide are even more preferable; tin(II) 2-ethylhexanoate, tin(II) stearate, and tin(II) oxide are even more preferable; and tin(II) octanoate and tin(II) 2-ethylhexanoate are even more preferable, from the viewpoint of the effect of an initial rise of charging of the toner and catalytic ability.

The titanium catalyst is preferably a titanium compound having a Ti—O bond, and the titanium compound having an alkoxy group (alkyloxy group), an alkenyloxy group, or an acyloxy group, each having 2 to 28 carbon atoms, is more preferable. The effects of the promoter of the present invention are more remarkably exhibited in a case of using a titanium compound represented by the formula (A):

$$\text{Ti}(X)_n(Y)_m \quad\quad (A)$$

wherein X is a substituted amino group having 4 go 8 carbon atoms; Y is a substituted or unsubstituted, alkoxy group having 2 to 28 carbon atoms, a substituted or unsubstituted, alkenyloxy group having 2 to 28 carbon atoms, or a substituted or unsubstituted, acyloxy group having 2 to 28 carbon atoms, and preferably an alkoxy group; and each of n and m is an integer of from 1 to 3, wherein the sum of n and m is 4; and/or a titanium compound represented by the formula (B):

$$\text{Ti}(Z)_4 \quad\quad (B)$$

wherein Z is a substituted or unsubstituted, alkoxy group having 2 to 28 carbon atoms, a substituted or unsubstituted, alkenyloxy group having 2 to 28 carbon atoms, or a substituted or unsubstituted, acyloxy group having 2 to 28 carbon atoms.

The titanium compound may be used alone or in admixture of two or more compounds.

However, if a specified titanium compound is used as a catalyst, there is a disadvantage that the reaction time becomes extremely long. For example, if a resin obtained by using a titanium compound represented by the formula (A) is used as a resin binder for a toner, an amino group of the titanium compound causes a certain effect after the deactivation, thereby leading to a disadvantage that the triboelectric chargeability of the toner is lowered.

Specifically, while a titanium compound, especially a titanium compound represented by the formula (A), has a very high initial catalytic activity, the titanium compound is disadvantageous in that its deactivation is very fast. Therefore, as compared to the conventionally used dibutyltin oxide, while the catalytic activity function at the initial stage of the reaction is high, the sustenance of the activity is weak, so that the reaction time becomes extremely long. However, although not wanting to be limited by theory, the reasons are unclear but are presumably as follows. By allowing the above-mentioned pyrogallol compound to coexist, the lowering of the catalytic activity of the titanium compound represented by the formula (A) is suppressed, and a high catalytic activity can be maintained, whereby the reaction time can be shortened.

Consequently, a polycondensation resin having a shorter heat history is obtained, and an increase in a low-molecular weight component or a volatile organic component can also be prevented by the shortening of the reaction time. Regarding the disadvantage in the triboelectric chargeability upon using the resin obtained by using a titanium compound represented by the formula (A) as a resin binder for a toner, the polycondensation resin of the present invention obtained by using together the above-mentioned pyrogallol compound can maintain excellent triboelectric chargeability of the toner, even when the polycondensation resin is used as a resin binder for a toner.

In the formula (A), it is preferable that the substituted amino group represented by X has 6 carbon atoms. Here, the substituted amino group in the present invention refers to a group containing a nitrogen atom which can be directly bond to a titanium atom, and the substituted amino group includes alkylamino groups which may have a hydroxyl group, a quaternary cationic group having a quaternary amino group, and the like, and the quaternary cationic group is preferred. The amino group can be formed by reacting, for example, a titanium halide with an amine compound, and the amine compound includes alkanolamine compounds such as monoalkanolamine compounds, dialkanolamine compounds, and trialkanolamine compounds; alkylamine compounds such as trialkylamine; and the like. Among them, the alkanolamines are preferred, and the trialkanolamine compounds are more preferred.

In addition, the group represented by Y has preferably from 2 to 10 carbon atoms, and more preferably from 2 to 5 carbon atoms.

Further, it is preferable that the group represented by X has a larger number of carbon atoms than the group represented by Y, from the viewpoint of the effects of the present invention, and the difference in the number of carbon atoms is preferably from 1 to 6, and more preferably 2 to 4.

Specific examples of the titanium compound represented by the formula (A) include titanium diisopropylate bis(triethanolaminate) [$Ti(C_6H_{14}O_3N)_2(C_3H_7O)_2$], titanium diisopropylate bis(diethanolaminate) [$Ti(C_4H_{10}O_2N)_2(C_3H_7O)_2$], titanium dipentylate bis(triethanolaminate) [$Ti(C_6H_{14}O_3N)_2(C_5H_{11}O_2)$], titanium diethylate bis(triethanolaminate) [$Ti(C_6H_{14}O_3N)_2(C_2H_5O)_2$], titanium dihydroxyoctylate bis(triethanolaminate) [$Ti(C_6H_{14}O_3N)_2(OHC_8H_{16}O)_2$], titanium distearate bis(triethanolaminate) [$Ti(C_6H_{14}O_3N)_2(C_{18}H_{37}O)_2$], titanium triisopropylate triethanolaminate [$Ti(C_6H_{14}O_3N)(C_3H_7O)_3$], titanium monopropylate tris(triethanolaminate) [$Ti(C_6H_{14}O_3N)_3(C_3H_7O)_1$], and the like. Among them, titanium diisopropylate bis(triethanolaminate), titanium diisopropylate bis(diethanolaminate) and titanium dipentylate bis(triethanolaminate) are preferable, which are available as marketed products, for example, of Matsumoto Trading Co., Ltd.

On the other hand, if a titanium compound represented by the formula (B) is used as a catalyst, the reaction time becomes extremely long, so that there is a disadvantage in the coloration of the resin. In addition, if a resin obtained by using a titanium compound represented by the formula (B) is used as a resin binder for a toner, there is a disadvantage in worsening of the image quality.

In other words, the titanium compound represented by the formula (B) does not have a high catalytic activity as in the conventionally used dibutyltin oxide, and the reaction time becomes long, while the titanium compound has excellent sustainability, so that the synthesis of the resin can be carried out. For this reason, the coloration of the resin or the causation of turbidity are likely to take place due to the decomposition of the monomer components by an extremely long duration of the reaction. If fixed images are formed with a toner obtained by using a resin suffering from coloration as described above, there give the results of worsened image quality (color), which is especially notable in a yellow toner which is more likely to be influenced by the color of the resin. However, if a polycondensation resin obtained by using a titanium compound represented by the formula (B) is used as a resin binder for a toner, there is a disadvantage that background fogging is more likely to take place. However, because of the coexistence of the above-mentioned pyrogallol compound, an increase in a low-molecular weight component or a volatile organic component can be prevented. In addition, with the shortening of the reaction time, a polycondensation resin having a shorter heat history can also be obtained. Although not wanting to be limited by theory, the reasons therefor are unclear, but are presumably as follows. By allowing the above-mentioned pyrogallol compound to coexist, the lowering of the catalytic activity of the titanium compound is suppressed, and a high catalytic activity is maintained.

In the formula (B), the group represented by Z has preferably from 8 to 22 carbon atoms, and more preferably from 16 to 20 carbon atoms, from the viewpoint of coloration and background fogging.

In addition, each of the groups represented by Z may be identical or different, and it is preferable that all the four groups of Z are an identical group, from the viewpoint of reaction activity and hydrolytic resistance.

Specific examples of the titanium compound represented by the formula (B) include tetra-n-butyl titanate [$Ti(C_4H_9O)_4$], tetrapropyl titanate [$Ti(C_3H_7O)_4$], tetrastearyl titanate [$Ti(C_{18}H_{37}O)_4$], tetramyristyl titanate [$Ti(C_{14}H_{29}O)_4$], tetraoctyl titanate [$Ti(C_8H_{17}O)_4$], dioctyl dihydroxyoctyl titanate [$Ti(C_8H_{17}O)_2(OHC_8H_{16}O)_2$], dimyristyl dioctyl titanate [$Ti(C_{14}H_{29}O)_2(C_8H_{17}O)_2$], and the like. Among them, tetrastearyl titanate, tetramyristyl titanate, tetraoctyl titanate and dioctyl dihydroxyoctyl titanate are preferable. These titanium compounds can be obtained by, for example, reacting a titanium halide with a corresponding alcohol, and are also available as marketed products of Nisso, or the like.

Here, in the formula (A) and the formula (B), the group represented by Y and the group represented by Z is unsubstituted or substituted with a substituent such as a hydroxyl group or a halogen, and those groups that are unsubstituted or substituted with a hydroxyl group are preferred, and those groups that are unsubstituted are more preferred.

A representative example of a polycondensation reaction in which the promoter of the present invention is used together with a catalyst includes a reaction of forming a polycondensation resin unit, such as a polyester unit having an ester bond (—COO—) formed by dehydration condensation of a carboxyl group and a hydroxyl group, a polyamide unit having an amide bond (—CONH—) formed by dehydration condensation of a carboxyl group and an amino group, a polyester-polyamide unit having both of the ester bond and the amide bond, and the like. In the formation of the polycondensation resin unit having an ester bond, the effects of the promoter of the present invention are more remarkably exhibited. Here, in the present invention, the polycondensation reaction is not limited to a reaction between different raw material monomers but a monomer having different functional groups within one molecule, for example, a reaction of forming polylactic acid by dehydration condensation of lactic acid having a hydroxyl group and a carboxyl group is also encompassed in the polycondensation reaction.

As raw material monomers of the polyester unit, an alcohol component and a carboxylic acid component are usually used.

The alcohol component includes aromatic diols such as an alkylene oxide adduct of bisphenol A represented by the formula (II):

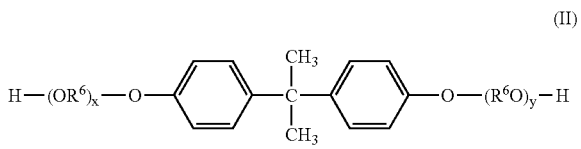

wherein $R^6O$ is an alkyleneoxy group, wherein $R^6$ is an alkylene group having 2 or 3 carbon atoms; and each of x and y is a positive number showing an average number of moles of alkylene oxide added, wherein the sum of x and y is from 1 to 16, and preferably from 1.5 to 5), such as polyoxypropylene-2,2-bis(4-hydroxyphenyl)propane and polyoxyethylene-2,2-bis(4-hydroxyphenyl)propane; aliphatic diols such as ethylene glycol, 1,2-propanediol, 1,3-propanediol, 1,4-butanediol, 1,5-pentanediol, 1,6-hexanediol, 1,4-butenediol, 1,3-butanediol, and neopentyl glycol; trihydric or higher polyhydric alcohols such as glycerol; and the like.

The carboxylic acid component include aliphatic dicarboxylic acids such as oxalic acid, malonic acid, maleic acid, fumaric acid, citraconic acid, itaconic acid, glutaconic acid, succinic acid, adipic acid, sebacic acid, azelaic acid, n-dodecylsuccinic acid, and n-dodecenylsuccinic acid; aromatic dicarboxylic acids such as phthalic acid, isophthalic acid, and terephthalic acid; alicyclic dicarboxylic acids such as cyclohexanedicarboxylic acid: tricarboxylic or higher polycarboxylic acids such as trimellitic acid and pyromellitic acid; and acid anhydrides of these acids, and alkyl(1 to 3 carbon atoms) esters of these acids; rosins; rosins modified with fumaric acid, maleic acid, acrylic acid or the like. The acids, anhydrides of these acids, and alkyl esters of the acids as mentioned above are collectively referred to herein as a carboxylic acid compound. In the present invention, the aromatic dicarboxylic acid compound is preferred, from the viewpoint of triboelectric chargeability. The aromatic dicarboxylic acid compound is contained in an amount of preferably 70% by mol or more, and more preferably 90% by mol or more, of the carboxylic acid component.

Here, the alcohol component may properly contain a monohydric alcohol, and the carboxylic acid component may properly contain a monocarboxylic acid compound, from the viewpoint of adjusting the molecular weight and improving offset resistance of the toner.

Further, raw material monomers for forming an amide bond in the polyester-polyamide unit or the polyamide unit include known various polyamines, aminocarboxylic acids, amino alcohols, and the like, and hexamethylenediamine and ε-caprolactam are preferred.

Here, the above raw material monomers may include those that are usually classified as monomers for open-ring polymerization, and these monomers are hydrolyzed due to the presence of water generated in the polycondensation reaction of other monomers, to be subject to polycondensation; therefore, these raw materials are also considered to be encompassed in the raw material monomers for a polycondensation resin in a broad sense.

The amount of the promoter of the present invention used in the polycondensation reaction is preferably from 0.001 to 1.0 parts by weight, more preferably from 0.005 to 0.4 parts by weight, and even more preferably from 0.01 to 0.2 parts by weight, based on 100 parts by weight of the raw material monomers used in the polycondensation reaction. The amount of the promoter used as referred to herein means an entire formulation amount of the promoter used in the polycondensation reaction.

On the other hand, the amount of the catalyst used is preferably from 0.01 to 2.0 parts by weight, more preferably from 0.1 to 1.5 parts by weight, and even more preferably from 0.2 to 1.0 part by weight, based on 100 parts by weight of the raw material monomers used in the polycondensation reaction. The amount of the catalyst used as referred to herein means an entire formulation amount of the catalyst used in the polycondensation reaction.

A weight ratio of the promoter to the catalyst, i.e. promoter/catalyst, is preferably from 0.01 to 0.5, more preferably from 0.03 to 0.3, and even more preferably from 0.05 to 0.2.

Here, in a case where a titanium compound represented by the formula (A) is used as a catalyst, the effects of the present invention can be obtained with a very small amount of the promoter; therefore, the amount of the above-mentioned pyrogallol compound (promoter of the present invention) in the polycondensation reaction used is preferably from 0.001 to 1.0 part by weight, more preferably from 0.002 to 0.5 parts by weight, even more preferably from 0.005 to 0.3 parts by weight, and even more preferably from 0.01 to 0.3 parts by weight, based on 100 parts by weight of the raw material monomers used in the polycondensation reaction. The amount of the pyrogallol compound used as referred to herein means an entire formulation amount of the pyrogallol compound used in the polycondensation reaction.

On the other hand, the amount of the titanium compound represented by the above-mentioned formula (A) used is preferably from 0.01 to 2.0 parts by weight, more preferably from 0.1 to 1.5 parts by weight, and even more preferably 0.2 to 1.0 part by weight, based on 100 parts by weight of the raw material monomers used in the polycondensation reaction. The amount of the titanium compound represented by the formula (A) used as referred to herein means an entire formulation amount of the titanium compound represented by the formula (A) used in the polycondensation reaction.

A weight ratio of the pyrogallol compound to the titanium compound represented by the formula (A), i.e. pyrogallol compound/titanium compound, is preferably from 0.001 to 0.5, more preferably from 0.005 to 0.3, and even more preferably from 0.01 to 0.2, from the viewpoint of shortening the polycondensation reaction time.

In addition, in a case where the titanium compound represented by the formula (B) is used as a catalyst, the amount of the above-mentioned pyrogallol compound (promoter of the present invention) used in the polycondensation reaction is preferably from 0.001 to 1.0 part by weight, more preferably from 0.01 to 0.5 parts by weight, and even more preferably from 0.02 to 0.3 parts by weight, based on 100 parts by weight of the raw material monomers used in the polycondensation reaction. The amount of the pyrogallol compound used as referred to herein means an entire formulation amount of the pyrogallol compound used in the polycondensation reaction.

On the other hand, the amount of the titanium compound represented by the above-mentioned formula (B) used is preferably from 0.01 to 2.0 parts by weight, more preferably from 0.1 to 1.5 parts by weight, and even more preferably 0.2 to 1.0 part by weight, based on 100 parts by weight of the raw material monomers used in the polycondensation reaction.

The amount of the titanium compound represented by the formula (B) used as referred to herein means an entire formulation amount of the titanium compound represented by the formula (B) used in the polycondensation reaction.

A weight ratio of the pyrogallol compound to the titanium compound represented by the formula (B), i.e. pyrogallol compound/titanium compound, is preferably from 0.01 to 0.5, more preferably from 0.02 to 0.3, and even more preferably from 0.05 to 0.2.

The polycondensation resin of the present invention is obtained by polycondensing raw material monomers in the same manner as in an ordinary polycondensation resin, except that the promoter of the present invention and the above-mentioned catalyst are used. For example, it is preferable that the polycondensation reaction is carried out at a temperature of from 180° to 250° C. in an inert gas atmosphere in the presence of a catalyst and a promoter of the present invention. The catalyst and the promoter may be previously mixed and added to a reaction system, or they may be separately added. In addition, the catalyst and the promoter may be previously mixed with a carboxylic acid component or an alcohol component, and added. The timing of adding the catalyst and the promoter to a reaction system may be either before the initiation of reaction or during the course of the reaction. It is preferable that the catalyst and the promoter are added at a time point before the reaction temperature is reached, from the viewpoint of obtaining an even more enhanced effect in the acceleration of the polycondensation reaction, and it is more preferable that they are added before the initiation of the reaction. In the present invention, before the initiation of the reaction as referred to herein means a state in which water formed in the polycondensation reaction has not yet been generated.

In the present invention, the polycondensation resin refers to a resin composed of a polycondensation resin unit, which includes not only a resin containing a polycondensation resin unit made of a polyester, a polyester-polyamide, a polyamide, or the like obtained by the above-mentioned polycondensation reaction, but also a hybrid resin containing two or more kinds of resin components including the above-mentioned polycondensation resin unit, for example, a hybrid resin in which a polycondensation resin unit and an addition polymerization resin unit are partially chemically bonded.

In addition, the polycondensation resin may be modified to an extent that the properties are substantially not impaired. For example, a modified polyester refers to a polyester grafted or blocked with phenol, urethane, epoxy, or the like according to a method described in JP-A-Hei-11-133668, JP-A-Hei-10-239903, JP-A-Hei-8-20636 or the like.

The polycondensation resin of the present invention can be used in various applications such as films, sheets, fibers, and toner materials for electrophotography, and the polycondensation resin can be suitably used as a resin binder for a toner for electrophotography.

The resin binder has a softening point of preferably from 90° to 160° C., more preferably from 95° to 155° C., and even more preferably from 98° to 150° C., from the viewpoint of fixing ability, storage property, and durability of the resulting toner. The resin binder has a glass transition temperature of preferably from 45° to 85° C., and more preferably from 50° to 80° C., from the same viewpoint. From the viewpoint of triboelectric chargeability and environmental stability, the resin binder has an acid value of preferably from 1 to 90 mgKOH/g, more preferably from 5 to 90 mgKOH/g, and even more preferably from 5 to 88 mgKOH/g, and a hydroxyl value of preferably from 1 to 80 mgKOH/g, more preferably from 8 to 60 mgKOH/g, and even more preferably from 8 to 55 mgKOH/g.

In the present invention, a toner for electrophotography containing the polycondensation resin of the present invention is further provided. In the toner, a known resin binder, for example, a vinyl resin such as styrene-acrylic resin, and other resins such as an epoxy resin, a polycarbonate, and a polyurethane may be used together within the range so as not to impair the effects of the present invention. The polycondensation resin of the present invention is contained in an amount of preferably 70% by weight or more, more preferably 80% by weight or more, even more preferably 90% by weight or more, and even more preferably essentially 100% by weight, of the resin binder.

The toner may further properly contain an additive such as a colorant, a releasing agent, a charge control agent, a magnetic powder, a fluidity improver, an electric conductivity modifier, an extender pigment, a reinforcing filler such as a fibrous material, an antioxidant, an anti-aging agent, or a cleanability improver.

As the colorant, all of the dyes, pigments and the like which are used as colorants for toners can be used, and carbon blacks, Phthalocyanine Blue, Permanent Brown FG, Brilliant Fast Scarlet, Pigment Green B, Rhodamine-B Base, Solvent Red 49, Solvent Red 146, Solvent Blue 35, quinacridone, carmine 6B, isoindoline, disazoyellow, or the like can be used. In the present invention, the toner may be any of black toner and color toner. The colorant is contained in an amount of preferably from 1 to 40 parts by weight, and more preferably from 2 to 10 parts by weight, based on 100 parts by weight of the resin binder.

The toner for electrophotography may be a toner obtained by any of conventionally known methods such as a melt-kneading method, an emulsion phase-inversion method, and a polymerization method, and a pulverized toner produced by the melt-kneading method is preferable, from the viewpoint of productivity and dispersibility of a colorant. In the case of a pulverized toner produced by the melt-kneading method, the toner can be produced, for example, by homogeneously mixing raw materials such as a resin binder, a colorant, and a charge control agent with a mixer such as a Henschel mixer, thereafter melt-kneading the mixture with a closed kneader, a single-screw or twin-screw extruder, an open roller-type kneader, or the like, cooling, pulverizing, and classifying the product. On the other hand, a toner produced by the polymerization method is preferable, from the viewpoint of forming a toner having a small particle size.

In addition, in a case where a polycondensation resin of the present invention obtained using the above-mentioned tin(II) compound without containing a Sn—C bond as a catalyst is used, a toner can also be obtained by a method including the step of preparing a resin dispersion for a toner containing resin particles containing the polycondensation resin, and aggregating and unifying the resin particles in the resin dispersion.

If a polycondensation resin obtained using a tin(II) compound without containing a Sn—C bond as a catalyst is dispersed in an organic solvent, the resin particles are not formed into particles having smaller sizes and give a broad particle size distribution. Although not wanting to be limited by theory, one of the causations therefor are presumably due to a structural change of the catalyst. In other words, it is presumed that if the above-mentioned polycondensation resin is dissolved in an organic solvent, white precipitates are deposited, so that the solution turns to be white turbid; for this reason, a structural change takes place in a part of the catalyst during the polymerization in the presence of the tin(II) compound without containing a Sn—C bond, and the remnants remaining in the resin obtained impede the control of the particle sizes and the particle size distribution of the resin particles. However, in the polycondensation of the raw material monomers, a polycondensation resin obtained by using a pyrogallol compound as a promoter in coexistence with a tin(II) compound without containing a Sn—C bond does not form any precipitates even when dissolved in an organic solvent, whereby resin particles containing a polycondensation resin having small particle sizes and a sharp particle size distribution are formed. This is presumably due to the fact that the pyrogallol compound used as a promoter can control a structural change of a tin(II) compound without containing a Sn—C bond. Moreover, a toner obtained by aggregating and unifying these resin particles in a resin dispersion has excellent transferability, so that an effect that the toner has excellent image properties is exhibited.

Further, even in a case where a polycondensation resin obtained by polycondensing raw material monomers using a tin(II) compound without containing a Sn—C bond and the above-mentioned pyrogallol compound is dispersed in an aqueous medium, resin particles having small particle sizes and a sharp particle size distribution can be obtained, and the toner obtained by aggregating and unifying the resin particles has excellent transferability, so that the toner has excellent image properties.

The above-mentioned resin dispersion is preferably a resin dispersion obtained by a method including the step of dispersing resin particles containing a polycondensation resin in an aqueous medium, and a method for producing the resin dispersion is not particularly limited thereto. The method for producing a resin dispersion includes, for example, a method including the step of forming resin particles containing a polycondensation resin in the presence of a nonionic surfactant in an aqueous medium (method a); a method including the steps of introducing an aqueous medium into a mixed solution prepared by dissolving or dispersing a polycondensation resin in an organic solvent, removing the organic solvent therefrom, and dispersing self-dispersible water-based resin particles (method b); a method including the steps of emulsion-polymerizing a radically polymerizable monomer solution prepared by dissolving a polycondensation resin, to give resin particles, and emulsifying these resin particles in an aqueous medium (method c); a method including the step of dispersing a thermally molten polycondensation resin in an aqueous medium without containing an organic solvent, while maintaining a molten state of the resin (method d); and the like. The method a and the method b are more preferred.

Here, in the present invention the aqueous medium may contain a solvent such as an organic solvent, and the aqueous medium contains water in an amount of preferably 50% by weight or more, more preferably 70% by weight or more, even more preferably 90% by weight or more, and even more preferably 99% by weight or more. In the polycondensation resin in the present invention, the polycondensation resin can be formed into fine particles by using only water without using an organic solvent, but on the other hand, the precipitates are not deposited even when the polycondensation resin is dissolved in an organic solvent. Therefore, the polycondensation resin can be suitably used not only in a method of obtaining a resin dispersion without using an organic solvent as described in the method a, but also in the method where use of an organic solvent is essential in the production process as described in the method b, c, or d. Here, in a case where an organic solvent is used, the organic solvent is preferably methyl ethyl ketone, tetrahydrofuran, toluene, ethyl acetate, or the like, taking the solubility of the resin into consideration.

The method a and the method b will be further described hereinbelow.

[Method a]

According to the method a, a polycondensation resin can be formed into fine particles by mixing a polycondensation resin and a nonionic surfactant to lower the viscosity of the mixture. Although not wanting to be limited by theory, this is presumably due to the following. The lowering of the viscosity of the mixture serves to make the resin compatible with the nonionic surfactant, thereby lowering an apparent softening point of the resin. Utilizing this phenomenon, an apparent softening point of a polycondensation resin which is made compatible with a nonionic surfactant can be lowered to a temperature equal to or lower than the boiling point of water. Even in a polycondensation resin alone having a melting point or a softening point of 100° C. or more, a resin dispersion prepared by dispersing emulsion particles of a resin containing a polycondensation resin in water can be obtained by adding water dropwise under a normal pressure. Since this method can be carried out with at least water and a nonionic surfactant, the method can also be applied to a resin insoluble in an organic solvent, and facility loads for collecting an organic solvent and maintaining an operating environment are not necessary, and specialized apparatuses that are necessitated when utilizing a mechanical means are unnecessary; therefore, there is an advantage that the resin dispersion can be economically produced.

The nonionic surfactant includes, for example, polyoxyethylene alkyl aryl ethers or polyoxyethylene alkyl ethers, such as polyoxyethylene nonyl phenyl ether, polyoxyethylene oleyl ether, and polyoxyethylene lauryl ether; polyoxyethylene sorbitan esters, such as polyoxyethylene sorbitan monolaurate and polyoxyethylene sorbitan monostearate; polyoxyethylene fatty acid esters, such as polyethylene glycol monolaurate, polyethylene glycol monostearate, and polyethylene glycol monooleate; oxyethylene/oxypropylene block copolymers; and the like. In addition, an anionic surfactant or a cationic surfactant may be used together with the nonionic surfactant.

As a nonionic surfactant, it is preferable that a nonionic surfactant having an excellent compatibility with the resin is selected. In order to obtain a stable dispersion of a polycondensation resin, it is preferable that the nonionic surfactant has a HLB of from 12 to 18, and it is more preferable that two or more nonionic surfactants having different HLBs are used depending upon the kinds of the resin.

The amount of the nonionic surfactant used, based on 100 parts by weight of the polycondensation resin, is preferably 5 parts by weight or more, from the viewpoint of lowering a melting point of the polycondensation resin, and the amount is preferably 80 parts by weight or less, from the viewpoint of controlling the nonionic surfactant remaining in the toner. Therefore, from the viewpoint of satisfying both of these viewpoints, the amount of the nonionic surfactant used is preferably from 5 to 80 parts by weight, more preferably from 10 to 70 parts by weight, and even more preferably from 20 to 60 parts by weight, based on 100 parts by weight of the polycondensation resin.

Upon the formation of the resin particles containing a polycondensation resin in an aqueous medium in the presence of the nonionic surfactant, it is desired that the temperature inside the system is kept within a range of from 10° C. above to 10° C. below a cloud point of the nonionic surfactant, preferably within a range of from 8° C. above to 8° C. below the cloud point, and more preferably within a range of from 5° C. above to 5° C. below the cloud point, from the viewpoint of dispersibility of the nonionic surfactant and prevention of the dispersion efficiency from being lowered.

For example, it is preferable that an aqueous medium, preferably deionized water or distilled water, is added dropwise to a mixture of a polycondensation resin and a nonionic surfactant in the state that a mixture is prepared by stirring to give a homogeneous mixture in the system. Here, in a case where a colorant is used, it is preferable that a polycondensation resin containing a colorant compatible with a nonionic surfactant is not separated from water.

The amount of the aqueous medium used is preferably from 100 to 3,000 parts by weight, more preferably from 400 to 3,000 parts by weight, and even more preferably from 800 to 3,000 parts by weight, based on 100 parts by weight of the polycondensation resin, from the viewpoint of obtaining homogeneous aggregated particles in subsequent steps.

Here, in a case where a polycondensation resin has an acidic group such as a carboxyl group or a sulfonic acid group, water may be added after neutralizing, or while neutralizing, all or a part of the polycondensation resin. In a case where a polycondensation resin having an acidic group is used, in addition to the factor of the nonionic surfactant, the self-emulsifiability of the resin serves as a controlling factor for particle sizes of the resin particles.

A dispersant can be used for the purpose of lowering a melt viscosity and a melting point of the polycondensation resin, and improving dispersibility of the resin particles formed. The dispersant includes, for example, water-soluble polymers, such as polyvinyl alcohol, methyl cellulose, ethyl cellulose, hydroxyethyl cellulose, and carboxymethyl cellulose; anionic surfactants such as sodium dodecylbenzenesulfonate and sodium octadecylsulfate; cationic surfactants such as laurylamine acetate, stearylamine acetate, and lauryltrimethylammonium chloride; amphoteric surfactants such as lauryldimethylamine oxide; and inorganic salts such as calcium triphosphate, aluminum hydroxide, calcium sulfate, and calcium carbonate. The amount of the dispersant used is preferably 20 parts by weight or less, more preferably 15 parts by weight or less, and even more preferably 10 parts by weight or less, based on 100 parts by weight of the polycondensation resin, from the viewpoint of emulsion stability and detergency.

The solid content inside the system for preparing a resin dispersion is preferably from 7 to 50% by weight, more preferably from 7 to 40% by weight, and even more preferably from 10 to 30% by weight, from the viewpoint of stability of the dispersion and handleability of the dispersion in the aggregating step. Here, the solid content includes non-volatile components such as a resin and a nonionic surfactant.

[Method b]

According to the method b, a resin dispersion containing self-dispersible water-based resin particles is obtained by, for example, dissolving a polycondensation resin in an organic solvent, adding a neutralizing agent thereto to ionize an acid group of the polycondensation resin, subsequently adding water thereto, and distilling off the organic solvent to phase-convert to an aqueous system. More specifically, a resin dispersion is obtained by, for example, furnishing a reactor equipped with a stirrer, a reflux condenser, a thermometer, a dropping funnel, and a nitrogen gas inlet tube, adding a neutralizing agent or the like to a polycondensation resin dissolved in an organic solvent to ionize an acid group (unnecessary in a case where the group is already ionized), subsequently adding water thereto, and thereafter distilling off the organic solvent to phase-convert to an aqueous system.

The dissolving of the polycondensation resin in an organic solvent and the adding of a neutralizing agent are usually carried out at a temperature of equal to or lower than a boiling point of a solvent, especially an organic solvent. Also, water used in this method includes, for example, ion-exchanged water, and the like.

The organic solvent is preferably a ketone-based solvent, from the viewpoint of emulsifiability, the ketone-based solvent including, for example, acetone, methyl ethyl ketone, diethyl ketone, dipropyl ketone, methyl isobutyl ketone, methyl isopropyl ketone, and the like, and methyl ethyl ketone is preferred.

In addition, the neutralizing agent includes, for example, an aqueous ammonia, an aqueous solution of alkalis such as sodium hydroxide, amines such as allylamine, isopropylamine, diisopropylamine, ethylamine, diethylamine, triethylamine, 2-ethylhexylamine, 3-ethoxypropylamine, diisobutylamine, 3-diethylaminopropylamine, tri-n-octylamine, t-butylamine, sec-butylamine, propylamine, methylaminopropylamine, dimethylaminopropylamine, n-propanolamine, butanolamine, 2-amino-4-pentanol, 2-amino-3-hexanol, 5-amino-4-octanol, 3-amino-3-methyl-2-butanol, monoethanolamine, isopropanolamine, neopentanolamine, diglycolamine, ethylenediamine, 1,3-diaminopropane, 1,2-diaminopropane, 1,6-diaminohexane, 1,9-diaminononane, 1,12-diaminododecane, a dimer fatty acid diamine, 2,2,4-trimethylhexamethylenediamine, 2,4,4-trimethylhexamethylenediamine, hexamethylenediamine, N-aminoethylpiperazine, N-aminopropylpiperazine, N-aminopropyldipiperidipropane, and piperazine; and the like. The amount of these neutralizing agents used may be an amount that can neutralize at least an acid value of the polycondensation resin.

The water-based resin particles in the resin dispersion thus obtained have a number-molecular weight of preferably from 2,500 to 70,000.

In a case where a toner is produced using the resin dispersion in the present invention, the resin particles have a volume-average particle size ($D_4$) of preferably from 0.05 to 3 μm, more preferably from 0.05 to 1 μm, and even more preferably from 0.05 to 0.8 μm, from the viewpoint of homogeneously aggregating the resin particles. In the present invention, the volume-average particle size ($D_4$) of the resin particles means an average particle size on volume percentage (proportion of the volume occupying particles having a given particle size to the volume of the entire particles), and the volume-average particle size can be measured with a laser diffraction particle size analyzer, or the like.

Upon the production of a toner using the above-mentioned resin dispersion, toner raw materials other than the resin dispersion, an additive, such as a colorant or a charge control agent, may be previously mixed with a polycondensation resin upon the preparation of the resin dispersion, and a dispersion in which each additive is separately dispersed in a dispersion medium such as water is prepared, and mixed with resin particles to be subject to an aggregating step. Upon the preparation of the resin particles, in a case where an additive is previously mixed with a polycondensation resin, it is preferable that the polycondensation resin and the additive are previously melt-kneaded. In the melt-kneading, it is preferable to use an open roller twin-screw kneader. The open-roller twin-screw kneader is a kneader containing two rollers arranged in parallel closely to each other, wherein a heating function or a cooling function can be provided by passing a medium for heating or cooling through each roller. Therefore, the open-roller type twin-screw kneader contains a melt-kneading part that is open, and also is equipped with a heat roller and a cooling roller, so that the open-roller type twin-screw kneader can easily dissipate the kneading heat generated during the melt-kneading, which is different from twin-screw extruders conventionally used.

The solid content in the system in the aggregating step for aggregating resin particles can be adjusted by adding water to a dispersion containing a polycondensation resin. The solid content in the system is preferably from 5 to 50% by weight, more preferably from 5 to 30% by weight, and even more preferably from 5 to 20% by weight, in order that a homogeneous aggregation is allowed to take place.

The pH inside the system in the aggregating step is preferably from 2 to 10, more preferably from 2 to 9, and even more preferably from 3 to 8, from viewpoint of satisfying both dispersion stability of the liquid mixture and aggregating property of fine particles of the polycondensation resin or the like.

From the same viewpoint, the temperature inside the system in the aggregating step is preferably a temperature between a temperature equal to higher than a temperature calculated from a softening point of the polycondensation resin minus(−) 60° C. and a temperature equal to or lower than the softening point of the polycondensation resin.

Here, upon the aggregation of the resin particles, not only the resin particles alone may be aggregated (homoaggregation), but also the dispersion of the resin particles may be mixed with a dispersion or the like of other fine resin particles obtained in the same manner as in the resin dispersion in the present invention, to aggregate the resin particles and the other fine resin particles (heteroaggregation).

In the aggregating step, in order to effectively aggregate the particles, an aggregating agent can be added. As the aggregating agent, an organic aggregating agent such as a cationic surfactant of a quaternary salt, or polyethyleneimine; an inorganic aggregating agent such as an inorganic metal salt or a divalent or higher polyvalent metal complex; or the like can be used. The inorganic metal salt includes, for example, metal salts, such as sodium sulfate, sodium chloride, calcium chloride, calcium nitrate, barium chloride, magnesium chloride, zinc chloride, aluminum chloride, and aluminum sulfate; and inorganic metal salt polymers, such as poly(aluminum chloride), poly(aluminum hydroxide), and calcium polysulfide.

The amount of the aggregating agent used is preferably 30 parts by weight or less, more preferably 20 parts by weight or less, and even more preferably 10 parts by weight or less, based on 100 parts by weight of the polycondensation resin, from the viewpoint of environmental resistance of the toner.

It is preferable that the aggregating agent is added after dissolving the aggregating agent in an aqueous medium, and it is preferable that the mixture is sufficiently stirred during the addition or after the termination of the addition of the aggregating agent.

Subsequently, aggregated particles containing at least a polycondensation resin obtained in the above-mentioned aggregating step is heated and unified (unifying step).

The temperature inside the system in the unifying step is preferably between a temperature equal to or higher than a temperature calculated from a softening point minus(−) 30° C. and a temperature equal to or lower than a temperature calculated from a softening point plus(+) 10° C., preferably between a temperature equal to or higher than a temperature calculated from a softening point minus(−) 25° C. and a temperature equal to or lower than a temperature calculated from a softening point plus(+) 10° C., and even more preferably between a temperature equal to or higher than a temperature calculated from a softening point minus(−) 20° C. and a temperature equal to or lower than a temperature calculated from a softening point plus(+) 10° C., from the viewpoint of particle sizes, particle size distribution, and shaping control of the intended toner, and fusibility of the particles.

The resulting unified particles are appropriately subjected to a solid-liquid separation step, such as filtration, a washing step, and a drying step, whereby a toner can be obtained.

In the washing step, for the purpose of securing sufficient triboelectric properties and reliability of the toner, it is preferable to use an acid for removing metal ions on the toner surface. In addition, the nonionic surfactant previously added is preferably completely removed by washing, and a washing with an aqueous solution at a temperature of equal to or lower than a cloud point of a nonionic surfactant is preferred. It is preferable that washings are carried out a plural times.

In addition, in the drying step, a given method, such as a vibrating fluidized bed drying method, a spray-drying method, a freeze-drying method, or a flash jet method can be employed. It is preferable that the water content of the toner after drying is adjusted to preferably 1.5% by weight or less, and more preferably 1.0% by weight or less, from the viewpoint of triboelectric properties.

The toner obtained by various methods described above has a volume-median particle size ($D_{50}$) of preferably from 3 to 15 μm, and more preferably from 3 to 10 μm. The volume-median particle size ($D_{50}$) as referred to herein means a particle size at 50% counting from smaller particle sizes in a cumulative volume frequency calculated in volume percentage. An external additive such as hydrophobic silica may be added to the surface of the toner.

The resulting toner can be used as a toner for monocomponent development, or as a two component developer prepared by mixing the toner with a carrier.

Second Embodiment

A second embodiment of the present invention is a method for producing a polycondensation resin including the step of subjecting raw material monomers to a polycondensation reaction using a metal-containing catalyst and a compound having a benzene ring of which at least two hydrogen atoms are substituted by hydroxyl groups, the method for producing a polycondensation reaction including the step of adding a phosphorus-containing compound to a reaction system at a point where a reaction ratio of the above-mentioned polycondensation reaction is 30% or more. In a case where a metal-containing catalyst and a compound having a benzene ring of which at least two hydrogen atoms are substituted by hydroxyl groups are used, by adding a phosphorus-containing compound thereto during the course of the polycondensation reaction, a polycondensation resin having a narrow molecular weight distribution (softening point distribution) can be obtained, while controlling the reaction rate, as necessary.

Specifically, the compound having a benzene ring of which at least two hydrogen atoms are substituted by hydroxyl groups, such as gallic acid, is capable of very highly enhancing the reactivity of a metal-containing catalyst with a small amount, so that a very high catalytic activity not conventionally found is obtained. However, because of its high reactivity, in a case where a crosslinking reaction takes place in a latter half of the reaction, there are some disadvantages as follows. It would be difficult to the control the crosslinking reaction. The effects are found with a small amount; therefore, if the catalyst remains in a reaction vessel even in a small amount, the reaction rate in the production of the polycondensation resin in the next batch would be undesirably influenced. In an actual field work, a certain period of time is necessitated in drawing out the resin from a reaction pot; however, the reaction progress even during the course of the draw-out, so that a resin having a broad molecular weight distribution (softening point distribution) would be produced.

As a result of studies, the inventors of the present invention have considered that the reason why the catalytic activity is enhanced is due to the fact that a compound having a benzene ring of which at least two hydrogen atoms are substituted by hydroxyl groups, such as gallic acid, is coordinated with a metal atom in the catalyst, and found a method of obtaining a polycondensation resin having a narrow molecular weight distribution (softening point distribution) by using a phosphorus-containing compound having an even higher coordination ability to a metal atom, thereby controlling the catalytic activity.

The feature of the present invention resides in that the method for producing a polycondensation resin includes the step of subjecting raw material monomers to a polycondensation reaction using a metal-containing catalyst, and a compound having a benzene ring of which at least two hydrogen atoms are substituted by hydroxyl groups (hereinafter simply referred to as "promoter"), the method including the step of adding a phosphorus-containing compound to a reaction system at a point where a polycondensation reaction reaches to a given reaction ratio or later, whereby the catalytic activity is deactivated in a latter half of the reaction, where necessary, so that the reaction rate can be controlled. Specifically, in the initial stage of reaction, it is considered that a promoter is coordinated with a metal atom, and the catalytic activity of a metal-containing catalyst is enhanced, so that the reaction is sufficiently accelerated; on the other hand, the catalytic activity can be deactivated by adding a phosphorus-containing compound thereto during the course of the reaction. This is presumably due to the fact that the phosphorus-containing compound has a higher coordination ability to a metal atom than the promoter. By the deactivation of the catalytic activity, the crosslinking reaction in the latter half of the reaction can be controlled, so that a polycondensation resin having a narrow molecular weight distribution (softening point distribution) can be obtained. In addition, the influences on the reaction rate of the next batch by the remnants of the catalyst in the reaction vessel and the progress of the reaction in the course of the draw-out from the reaction vessel can be prevented.

As the metal-containing catalyst, a compound preferably containing at least one metal selected from the group consisting of aluminum, antimony, tin, and titanium, and more preferably a compound containing tin or titanium, is desirable, from the viewpoint of catalytic activity.

The tin compound includes a tin compound having a Sn—C bond such as dibutyltin oxide, and a tin(II) compound without containing a Sn—C bond.

As the tin(II) without containing a Sn—C bond, a tin(II) compound having a Sn—O bond, a tin(II) compound having a Sn—X bond, wherein X is a halogen atom, or the like is preferable, and the tin(II) compound having a Sn—O bond is more preferable. The tin(II) having a Sn—O bond includes the same compounds as those given in the first embodiment.

The titanium compound is preferably a titanium compound having a Ti—O bond, and a compound having an alkyloxy group, an alkenyloxy group, or an acyloxy group, each having 1 to 28 carbon atoms, and preferably 2 to 28 carbon atoms, is more preferable.

The titanium compound includes a titanium compound represented by the formula (A) and a titanium compound represented by the formula (B), each exemplified in the first embodiment, and specific examples of those titanium compounds are the same compounds as those listed in the first embodiment.

As the aluminum compound, known aluminum compounds can be used without limitations. Specific examples thereof include carboxylates such as aluminum formate, aluminum acetate, basic aluminum acetate, aluminum propionate, aluminum oxalate, aluminum acrylate, aluminum laurate, aluminum stearate, aluminum benzoate, aluminum trichloroacetate, aluminum lactate, aluminum citrate, and aluminum salicylate; and inorganic acid salts such as aluminum chloride, aluminum hydroxide, poly(aluminum chloride), aluminum carbonate, aluminum phosphate, and aluminum phosphonate.

In addition, other aluminum compounds include aluminum alkoxides, such as aluminum methoxide, aluminum ethoxide, aluminum n-propoxide, aluminum isopropoxide, aluminum n-butoxide, and aluminum t-butoxide; aluminum chelating compounds such as aluminum acetylacetonate, aluminum acetylacetate, aluminum ethyl acetoacetate, and aluminum ethyl acetoacetate di-isopropoxide; organic aluminum-containing compounds such as trimethylaluminum and triethylaluminum, and partial hydrolysate thereof; aluminum oxide; and the like. Among them, the carboxylates, the inorganic salts, and the chelating compounds are preferred, among which further basic aluminum acetate, aluminum chloride, aluminum hydroxide, poly(aluminum chloride), and acetylacetonatoaluminum are more preferred.

As the antimony compound, a known antimony compound can be used without limitation. Specific examples thereof include antimony trioxide, antimony pentoxide, antimony acetate, antimony glycoxide, and the like. Among them, antimony trioxide is preferred.

The amount of the metal-containing catalyst used is preferably from 0.01 to 2.0 parts by weight, more preferably from 0.1 to 1.5 parts by weight, and even more preferably from 0.2 to 1.0 part by weight, based on 100 parts by weight of the raw material monomers used in the polycondensation reaction.

On the other hand, in the promoter, the compound having a benzene ring of which two hydrogen atoms are substituted by hydroxyl groups include dihydric phenols such as hydroquinone; phenolic compounds having at least a substituent at an ortho-position to the hydroxyl group (hereinafter simply referred to as a hindered phenol); and the like. Among them, a compound having a benzene ring of which two hydroxyl groups are adjacent to each other is preferred, from the viewpoint of improvement in catalytic activity.

The dihydric phenol means a compound in which two OH groups are bonded to a benzene ring, but other substituents are not bonded thereto, and hydroquinone is preferred.

The hindered phenol includes mono-t-butyl-p-cresol, mono-t-butyl-m-cresol, t-butyl catechol, 2,5-di-t-butyl hydroquinone, 2,5-di-t-amyl hydroquinone, propyl gallate, 4,4'-methylenebis(2,6-t-butylphenol), 4,4'-isopropylidenebis 2,6-di-t-butylphenol), 4,4'-butylidenebis(3-methyl-6-t-butylphenol), butylhydroxyanisole, 2,6-di-t-butyl-p-cresol, 2,6-di-t-butylphenol, 2,6-di-t-butyl-4-ethylphenol, 2,4,6-tri-t-butylphenol, octadecyl-3-(4-hydroxy-3',5'-di-t-butylphenyl) propionate, distearyl(4-hydroxy-3-methyl-5-t-butyl) benzyl malonate, 6-(4-hydroxy-3,5-di-t-butylanilino)-2,4-bisoctylthio-1,3,5-triazine, 2,6-diphenyl-4-octadecanoxyphenol, 2,2'-methylenebis(4-methyl-6-t-butylphenol), 2,2'-methylenebis(4-ethyl-6-t-butylphenol), 2,2'-isobutylidenebis 4,6-dimethylphenol), 2,2'-dihydroxy-3, 3'-di-(α-methylcyclohexyl)-5,5'-dimethyldiphenylmethane, 2,2'-methylenebis(4-methyl-6-cyclohexylphenol), tris[β-(3, 5-di-t-butyl-4-hydroxyphenyl)propionyloxyethyl]isocyanurate, 1,3,5-tris(2,6-dimethyl-3-hydroxy-4-t-butylbenzyl) isocyanurate, tris(3,5-di-t-butyl-4-hydroxyphenol) isocyanurate, 1,1,3'-tris(2-methyl-4-hydroxy-5-t-butylphenyl) butane, 2,6-bis(2'-hydroxy-3'-t-butyl-5'-methylbenzyl)-4-methylphenol, N,N'-hexamethylenebis(3,5-di-t-butyl-4-hydroxyhydrocinnamate), hexamethyleneglycolbis[β-(3,5-di-t-butyl-4-hydroxyphenyl)propionate], triethyleneglycolbis[β-(3-t-butyl-5-methyl-4-hydroxyphenyl)propionate], tetrakis[methylene-3-(3,5-di-t-butyl-4-hydroxyphenyl)propionate]methane, and the like. Among them, t-butyl catechol is preferred.

As the compound having a benzene ring of which at least two hydrogen atoms are substituted by hydroxyl groups, pyrogallol compounds having a benzene ring of which three hydrogen atoms adjacent to each other are substituted by hydroxyl groups are preferred, from the viewpoint of reaction activity of the polycondensation reaction due to the catalytic activity. Concrete examples of the pyrogallol compound include the same compounds as those given in the first embodiment.

The amount of the promoter used in the polycondensation reaction is preferably from 0.001 to 1.0 part by weight, more preferably from 0.005 to 0.4 parts by weight, and even more preferably from 0.01 to 0.2 parts by weight, based on 100 parts by weight of the raw material monomers used in the polycondensation reaction, from the viewpoint of catalytic activity.

A weight ratio of the promoter to the metal-containing catalyst, i.e. promoter/metal-containing catalyst, is preferably from 0.01 to 0.5, more preferably from 0.03 to 0.3, and even more preferably from 0.05 to 0.2, from the viewpoint of catalytic activity.

The amounts of the metal-containing catalyst and the promoter used in the polycondensation reaction mean the entire amounts of the metal-containing catalyst and the promoter used in the polycondensation reaction.

As the phosphorus-containing compound, organophosphorus compounds are preferred. The phosphorus-containing compound includes, for example, phosphonic acids selected from phosphonic acid, ethane-1,1-diphosphonic acid, ethane-1,1,2-triphosphonic acid, ethane-1-hydroxy-1,1-diphosphonic acid (1-hydroxyethylidene-1,1-diphosphonic acid), ethanehydroxy-1,1,2-triphosphonic acid, methanehydroxyphosphonic acid, ethane-1,2-dicarboxy-1,2-diphosphonic acid, butane-1,2-dicarboxy-2-phosphonic acid, butane-2,3,4-tricarboxy-1-phosphonic acid, propane-1,2-dicarboxy-2-phosphonic acid, and aminotrimethylenephosphonic acid, or alkali metal salts or alkanolamine salts thereof, and the like. Among them, phosphonic acid, 1-hydroxyethylidene-1,1-diphosphonic acid, aminotrimethylenephosphonic acid, and pentasodium aminotrimethylenephosphonate are preferred, from the viewpoint of the coordination to a metal atom.

A weight ratio of the phosphorus-containing compound to the metal-containing catalyst used, i.e. phosphorus-containing compound/metal-containing catalyst, is preferably from 0.05 to 4, more preferably from 0.1 to 2, and even more preferably from 0.2 to 1, from the viewpoint of obtaining a resin having controlled catalytic activity and a narrow distribution of softening points. In addition, from the same viewpoints, a weight ratio of the phosphorus-containing compound to the promoter used, i.e. phosphorus-containing compound/promoter, is preferably from 0.2 to 50, more preferably from 0.5 to 30, and even more preferably from 1 to 10.

The polycondensation reaction includes a reaction of forming a polycondensation resin unit, such as a polyester unit having an ester bond (—COO—) formed by dehydration condensation of a carboxyl group and a hydroxyl group, a polyamide unit having an amide bond (—CONH—) formed by dehydration condensation of a carboxyl group and an amino group, or a polyester-polyamide unit having both of the ester bond and the amide bond. In the formation of the polycondensation resin unit having an ester bond, the effects of the present invention are more remarkably exhibited. Here, in the present invention, the polycondensation reaction is not limited to a reaction between different raw material monomers but a monomer having different functional groups within one molecule, for example, a reaction of forming polylactic acid by dehydration condensation of lactic acid having a hydroxyl group and a carboxyl group is also encompassed in the polycondensation reaction.

As raw material monomers of the polyester unit, an alcohol component and a carboxylic acid component are usually used.

The alcohol component includes aromatic diols such as an alkylene oxide adduct of bisphenol A represented by the formula (III):

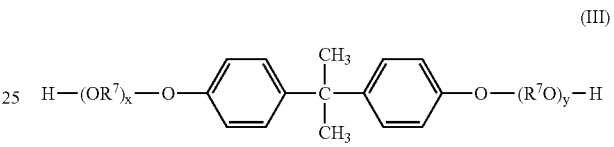

(III)

wherein $R^7O$ is an oxyalkylene group, wherein $R^7$ is an ethylene group and/or a propylene group; and each of x and y is a positive number showing an average number of moles of alkylene oxide added, wherein the sum of x and y is from 1 to 16, preferably from 1 to 8, and even more preferably from 1.5 to 4, such as polyoxypropylene-2,2-bis(4-hydroxyphenyl)propane and polyoxyethylene-2,2-bis(4-hydroxyphenyl)propane; aliphatic diols such as ethylene glycol, 1,2-propanediol, 1,3-propanediol, 1,4-butanediol, 1,5-pentanediol, 1,6-hexanediol, 1,4-butenediol, 1,3-butanediol, and neopentyl glycol; trihydric or higher polyhydric alcohols such as glycerol; and the like.

The carboxylic acid component include aliphatic dicarboxylic acids such as oxalic acid, malonic acid, maleic acid, fumaric acid, citraconic acid, itaconic acid, glutaconic acid, succinic acid, adipic acid, sebacic acid, azelaic acid, n-dodecylsuccinic acid, and n-dodecenylsuccinic acid; aromatic dicarboxylic acids such as phthalic acid, isophthalic acid, and terephthalic acid; alicyclic dicarboxylic acids such as cyclohexanedicarboxylic acid: tricarboxylic or higher polycarboxylic acids such as trimellitic acid and pyromellitic acid; and acid anhydrides of these acids, and alkyl(1 to 3 carbon atoms) esters of these acids; rosins; modified rosins modified with fumaric acid, maleic acid, or acrylic acid. The acids, anhydrides of these acids, and alkyl esters of the acids as mentioned above are collectively referred to herein as a carboxylic acid compound.

In the present invention, it is preferable that the carboxylic acid component contains an aromatic dicarboxylic acid compound, from the viewpoint of reactivity of the polycondensation reaction. The aromatic dicarboxylic acid compound is contained in an amount of preferably from 30 to 95% by mol, and more preferably from 50 to 80% by mol, of the carboxylic acid component.

In addition, since in the method of the present invention, the control of the crosslinking reaction is facilitated, it is preferable that a trivalent or higher polyvalent monomer is contained in the raw material monomer. As the trivalent or higher polyvalent monomers, tricarboxylic or higher polycarboxylic acid compounds are preferred, and trimellitic anhydride is more preferred, from the viewpoint of reaction activity. The tricarboxylic or higher polycarboxylic acid compound is contained in an amount of preferably from 5 to 50% by mol, and more preferably from 20 to 40% by mol, of the carboxylic acid component.

Here, the alcohol component may properly contain a monohydric alcohol, and the carboxylic acid component may properly contain a monocarboxylic acid compound, from the viewpoint of adjusting the molecular weight and improving offset resistance of the toner.

Further, raw material monomers for forming an amide bond in the polyester-polyamide unit or the polyamide unit include known various polyamines, aminocarboxylic acids, amino alcohols, and the like, and hexamethylenediamine and ε-caprolactam are preferred.

Here, the above raw material monomers may include those that are usually classified as monomers for open-ring polymerization, and these monomers are hydrolyzed due to the presence of water generated in the polycondensation reaction of other monomers, to be subject to polycondensation; therefore, these raw materials are also considered to be encompassed in the raw material monomers for a polycondensation resin in a broad sense.

The polycondensation reaction in the present invention can be carried out according to an ordinary method, except that a metal-containing catalyst and a promoter are used, and that a phosphorus-containing compound is added at a point where the reaction ratio of the polycondensation reaction is 30% or more, and preferably from 50 to 95%. For example, it is preferable that the polycondensation reaction of an alcohol component and a carboxylic acid component for forming a polyester unit is carried out at a temperature of from 180° to 250° C. in an inert gas atmosphere in the presence of the metal-containing catalyst and the promoter. The metal-containing catalyst and the promoter may be previously mixed and added to a reaction system, or they may be separately added. Here, the above-mentioned reaction ratio is a reaction ratio in the overall polycondensation reaction.

The timing of adding the metal-containing catalyst and the promoter to a reaction system may be either before the initiation of the reaction or during the course of the reaction, so long as the metal-containing catalyst and the promoter are added before adding a phosphorus-containing compound. The metal-containing catalyst and the promoter may be previously mixed with a carboxylic acid component or an alcohol component, and added. It is preferable that the metal-containing catalyst and the promoter are added at the initiation of the reaction.

On the other hand, the timing of adding a phosphorus-containing compound can be appropriately selected, so long as the reaction ratio in the overall polycondensation reaction reaches to a given value, from the viewpoint of deactivating the catalytic activity of the metal-containing catalyst and the promoter. In the present invention, it is preferable that a phosphorus-containing compound is added in a reaction where the polycondensation reaction is carried out in two or more steps of the reaction. The phrase "two or more steps of the reaction" refer to a method of feeding raw material monomers in two or more separate steps.

In a case of a two-step reaction, it is desired that raw material monomers fed in a first step are reacted at 50% or more, preferably 60% or more, more preferably 80% or more, and even more preferably 90% or more, and thereafter the remaining monomers are fed thereto. On the other hand, a method including the steps of feeding all of the raw material monomers in one instance, and reacting the raw material monomers is referred to as a one-step reaction. While the raw material monomers are linked randomly in a one-step reaction, the linkage of the monomers can be controlled to a certain extent by carrying out a two or more-step reaction, whereby increasing the degree of freedom of the design of the resin. Also, in a case where raw material monomers having different reactivity are used, the control of the reaction ratio or the like of each monomer would be difficult when reacted concurrently; on the other hand, the shortening of the reaction time and a high level of reaction control can be accomplished by previously reacting the raw material monomers having poor reactivity.

Therefore, in a reaction of two or more steps, it is preferable that raw material monomers different from those of the first step are fed in the second-step reaction, from the viewpoint of shortening the reaction time and controlling the reaction to obtain a resin having a narrow distribution of softening points. It is more preferable that raw material monomers requiring a high reaction activity, i.e. raw material monomers having a low reactivity, are fed in the first-step reaction, and raw material monomers requiring reaction control, for example, raw material monomers that greatly influence softening points of the resin are fed in the second- and subsequent-step reaction, respectively, and subsequently a phosphorus-containing compound is fed thereto during the course of the first-step reaction or the second or subsequent step. For example, in a case where an aromatic dicarboxylic acid compound and a tricarboxylic or higher polycarboxylic acid compound are used as a carboxylic acid component, it is desired that an alcohol component and a carboxylic acid component such as an aromatic dicarboxylic acid compound are fed in the first-step reaction, and that a phosphorus-containing compound is added at a point where a reaction ratio of the alcohol component to the aromatic dicarboxylic acid compound reaches to preferably 50% or more, more preferably 70% or more, and even more preferably 90% or more, from the viewpoint of efficiently carrying out the reactions by different raw material monomers having different reaction activities, and that the tricarboxylic or higher polycarboxylic acid compound is fed concurrently with the addition of the phosphorus-containing compound, or after the addition of the phosphorus-containing compound. The term "reaction ratio" as used herein refers to a value obtained by the formula:

$$\text{Reaction Ratio} = \frac{\text{Amount of Water Formed in Reaction(mol)}}{\text{Theoretical Amount of Water Formed(mol)}} \times 100$$

In the reaction of two or more steps, the timing of adding a phosphorus-containing compound is preferably from a period between 60 minutes before the termination of the first-step reaction and 30 minutes before the termination of the entire reaction, more preferably a period between 30 minutes before the termination of the first-step reaction and 45 minutes before the termination of the entire reaction, and even more preferably a period between the termination of the first-step reaction and the initiation of the second-step reaction, from the viewpoint of reaction control of the polycondensation reaction, and obtainment of a resin having a narrow distribution of softening points. The phrase "the termination of entire reaction" as used herein refers to a time point where the heating inside the system is stopped, and the draw-out of the resin from a reaction vessel obtained is started.

The polycondensation resin obtained by the present invention refers to a resin containing a polycondensation resin unit in the same manner as that described in the first embodiment, which may be subject to modification to an extent that would not substantially impair its property.

The polycondensation resin obtained by the present invention can be used in various applications, including, for example, films, sheets, fibers, and toner materials for electrophotography.

In a case where a polycondensation resin is used by thermally fusing or melt-kneading to disperse an additive therein, a low-temperature kneading does not sufficiently melt the resin, and dispersibility is insufficient because of a too high melt viscosity or the like, and in certain cases a part of a polymer chain is undesirably cut off, thereby undesirably leading to a low softening point, a low strength, or the like. Therefore, a certain level of a high-temperature kneading is desired at which point the melt viscosity is lowered is desired; however, upon kneading at a high temperature, there is a disadvantage that the polycondensation undesirably progresses, so that the used resin becomes a high softening point resin in a manufactured article.

By contrast, the polycondensation resin obtained by the method of the present invention has a well controlled reaction rate and a narrow molecular weight distribution (softening point distribution), so that the polycondensation resin is suitably used as a polycondensation resin for resin molding products or toner materials for electrophotography, in which a polycondensation resin is used by thermally fusing or melt-kneading raw material monomers at a temperature of preferably 120° C. or higher, more preferably 150° C. or higher, and even more preferably 180° C. or higher.

EXAMPLES

The following examples further describe and demonstrate embodiments of the present invention. The examples are given solely for the purposes of illustration and are not to be construed as limitations of the present invention.

[Softening Point of Resin]

The softening point refers to a temperature at which a half the amount of the sample flows out when plotting a downward movement of a plunger against temperature, as measured by using a flow tester (CAPILLARY RHEOMETER "CFT-500D," commercially available from Shimadzu Corporation), in which a 1 g sample is extruded through a nozzle having a diameter of 1 mm and a length of 1 mm while heating the sample so as to raise the temperature at a rate of 6° C./min and applying a load of 1.96 MPa thereto with the plunger.

[Glass Transition Temperature of Resin]

The glass transition temperature refers to a temperature of an intersection of the extension of the baseline of equal to or lower than the temperature of the endothermic highest peak and the tangential line showing the maximum inclination between the kick-off of the peak and the top of the peak, which is determined using a differential scanning calorimeter ("DSC 210," commercially available from Seiko Instruments, Inc.), by weighing out 0.01 to 0.02 g of the sample into an aluminum crucible, raising its temperature to 200° C., cooling the sample from this temperature to 0° C. at a cooling rate of 10° C./min, and thereafter raising the temperature of the sample at a heating rate of 10° C./min.

[Acid Value of Resin]

The acid value is determined by a method according to JIS K0070 except that only the determination solvent was changed from a mixed solvent of ethanol and ether as defined in JIS K0070 to a mixed solvent of acetone and toluene (volume ratio of acetone:toluene=1:1). Incidentally, the determination solvent was changed to chloroform, only for a series of Example III.

[Number-Average Molecular Weight of Resin]

The number-average molecular weight is determined by the gel permeation chromatography (concentration of the sample: 0.5% by weight, eluent: tetrahydrofuran, flow rate: 1 ml/min, and temperature: 40° C.). Here, a sample is prepared by charging a 20 ml sample tube with 40 mg of resin powder and 10 ml of chloroform, stirring the ingredients with a ball-mill at room temperature for 3 hours, and thereafter filtering the mixture with a membrane filter (commercially available from Toyo Roshi Kaisha, Ltd., pore size: 0.2 μm).

Here, using "GMHLX+G3000HXL" (commercially available from Tosoh Corporation) as a column, the calibration curve of the molecular weight is prepared by using several kinds of monodisperse polystyrenes (those having molecular weights of $2.63 \times 10^3$, $2.06 \times 10^4$, and $1.02 \times 10^5$, commercially available from Tosoh Corporation, and $2.10 \times 10^3$, $7.00 \times 10^3$, and $5.04 \times 10^4$, commercially available from GL Sciences Inc.) as standard samples.

[Melting Point of Wax]

The melting point refers to the maximum peak temperature for heat of fusion, which is determined using a differential scanning calorimeter ("DSC 210," commercially available from Seiko Instruments, Inc.), by raising its temperature to 200° C., cooling the sample from this temperature to 0° C. at a cooling rate of 10° C./min, and thereafter raising the temperature of the sample at a heating rate of 10° C./min.

[Particle Size of Resin Particles]

Using a laser diffraction particle size analyzer "LA-920" (commercially available from HORIBA, Ltd.), a cell for determination is charged with distilled water and a volume-average particle size ($D_4$) is determined at a concentration of the dispersion so that its absorbance is within a proper range. The particle size distribution is expressed as CV value (standard deviation of particle size distribution/volume-average particle size ($D_4$)×100).

[Volume-Median Particle Size ($D_{50}$) of Toner]

Measuring Apparatus Coulter Multisizer II (commercially available from Beckman Coulter K.K.)

Aperture Diameter: 50 μm

Analyzing Software: Coulter Multisizer AccuComp Ver. 1.19 (commercially available from Beckman Coulter K.K.)

Electrolytic solution: "Isotone II" (commercially available from Beckman Coulter K.K.)

Dispersion: A 5% electrolytic solution of "EMULGEN 109P" (commercially available from Kao Corporation, polyoxyethylene lauryl ether, HLB: 13.6)

Dispersion Conditions Ten milligrams of a test sample is added to 5 ml of the dispersion, and the resulting mixture is dispersed in an ultrasonic disperser for 1 minute. Thereafter, 25 ml of the electrolytic solution is added to the dispersion, and the resulting mixture is dispersed in the ultrasonic disperser for another 1 minute.

Measurement Conditions One-hundred milliliters of the electrolytic solution and the dispersion are added to a beaker, and the particle sizes of 30,000 particles are determined under the conditions of a concentration satisfying that the determination for 30,000 particles are completed in 20 seconds. The volume-median particle size ($D_{50}$) is obtained from the particle size distribution.

Examples I-1 to I-12, Comparative Examples I-1 to I-5, and Reference Examples I-1 and I-2

A 10-liter four-necked flask equipped with a nitrogen inlet tube, a dehydration tube, a stirrer, and a thermocouple was charged with 7,524 g of polyoxypropylene(2.05)-2,2-bis(4-hydroxyphenyl)propane (BPA-PO), 2,191 g of terephthalic acid (60 mol based on 100 mol of BPA-PO), and a catalyst and a promoter shown in Table I-1. The ingredients in the flask were subjected to a polycondensation reaction at 235° C. under a nitrogen gas atmosphere until the acid value reached to 15 mgKOH/g. The reaction time taken is shown in Table I-1.

TABLE I-1

|  | Catalyst[1] | Amount [X] (Parts by wt.) | Promoter[2] | Amount [Y] (Parts by wt.) | Y/X | Reaction Time (hr) |
|---|---|---|---|---|---|---|
| Ex. I-1 | S1 | 0.5 | P1 | 0.05 | 0.1 | 2.00 |
| Ex. I-2 | S1 | 0.5 | P2 | 0.05 | 0.1 | 2.50 |
| Ex. I-3 | S1 | 0.5 | P3 | 0.05 | 0.1 | 2.50 |
| Ex. I-4 | S1 | 0.5 | P4 | 0.05 | 0.1 | 2.25 |
| Ex. I-5 | S1 | 0.5 | P1 | 0.01 | 0.02 | 2.75 |
| Ex. I-6 | S1 | 0.5 | P1 | 0.1 | 0.2 | 2.50 |
| Ex. I-7 | S1 | 0.5 | P1 | 0.2 | 0.4 | 3.00 |
| Ex. I-8 | S1 | 0.3 | P1 | 0.05 | 0.17 | 2.50 |
| Ex. I-9 | S1 | 1.5 | P1 | 0.4 | 0.27 | 2.75 |
| Ex. I-10 | S1 | 0.1 | P1 | 0.4 | 4 | 5.25 |
| Ex. I-11 | S1 | 0.5 | P1 | 0.001 | 0.002 | 3.25 |
| Ex. I-12 | S2 | 0.5 | P1 | 0.05 | 0.1 | 3.50 |
| Comp. Ex. I-1 | S1 | 0.5 | — | — | — | 4.00 |
| Comp. Ex. I-2 | S1 | 0.1 | — | — | — | 6.00 |
| Comp. Ex. I-3 | S1 | 1.5 | — | — | — | 4.25 |
| Comp. Ex. I-4 | S1 | 0.5 | P5 | 0.05 | 0.1 | 4.00 |
| Comp. Ex. I-5 | S2 | 0.5 | — | — | — | 7.25 |
| Ref. Ex. I-1 | — | — | P1 | 0.05 | — | Not Reacted |
| Ref. Ex. I-2 | — | — | P3 | 0.05 | — | Not Reacted |

Note)
The amount (parts by wt.) of the catalyst and the promoter used is an amount based on 100 parts by weight of the raw material monomers.
[1] S1: Dibutyltin oxide S2: Titanium stearate
[2] P1: Pyrogallic acid P2: Octyl pyrogallate P3: Pyrogallol P4: 2,3,4-Trihydroxybenzophenone P5: Phloroglucinol (1,3,5-Trihydroxybenzene)

It can be seen from the above results that, as in Examples, the catalytic activity is increased and the reaction time is shortened because a pyrogallol compound is used as a promoter together with the catalyst in the polycondensation reaction.

Examples II-1 to II-20, Comparative Examples II-1 to II-11, and Reference Example II-1

A 10-liter four-necked flask equipped with a nitrogen inlet tube, a dehydration tube, a stirrer, and a thermocouple was charged with 6,840 g of polyoxypropylene(2.05)-2,2-bis(4-hydroxyphenyl)propane (BPA-PO), 2,600 g of terephthalic acid (87 mol based on 100 mol of BPA-PO), and a catalyst and a promoter shown in Table II-1. The ingredients in the flask were subjected to a polycondensation reaction at 235° C. under a nitrogen gas atmosphere until the acid value reached to 15 mgKOH/g. Thereafter, the reaction mixture was further reacted at 8 kPa until the softening point reached to 107° C., to give a polyester. The reaction time taken is shown in Table II-1.

One-hundred parts by weight of the resulting polyester, 4 parts by weight of a carbon black "MOGUL L" (commercially available from Cabot Corporation), 1 part by weight of a negative charge control agent "BONTRON S-34" (commercially available from Orient Chemical Co., Ltd.), and 2 parts by weight of a polypropylene wax "NP-105" (commercially available from MITSUI CHEMICALS, INC., melting point of 140° C.) were sufficiently mixed with a Henschel mixer. Thereafter, the mixture was melt-kneaded with a co-rotating twin-screw extruder having an entire length of the kneading portion of 1560 mm, a screw diameter of 42 mm and a barrel inner diameter of 43 mm at a rotational speed of the roller of 200 r/min, and a heating temperature within the roller of 80° C. The feeding rate of the mixture was 20 kg/hr, and the average residence time was about 18 seconds. The resulting melt-kneaded product was cooled and roughly pulverized, and thereafter pulverized with a jet mill and classified, to give a powder having a volume-median particle size ($D_{50}$) of 7.5 µm.

The amount 0.1 parts by weight of a hydrophobic silica "Aerosil R-972" (commercially available from Nippon Aerosil) was added as an external additive to 100 parts by weight of the resulting powder, and the mixture was mixed with a Henschel mixer, to give a toner.

The extent of aggregation of the resulting toner was determined by the following method using a powder tester (commercially available from Hosokawa Micron Corporation), and fluidity was evaluated in accordance with the evaluation criteria. The results are shown in Table II-1. Here, the extent of aggregation is an index showing powder fluidity in which the larger the number, the lower the fluidity of the powder.

[Aggregation]

Three sieves each having different sieve openings (250 µm, 149 µm, and 74 µm) are set on a vibration table of the powder tester in the order of 250 µm at an upper sieve, 149 µm at a middle sieve, and 74 µm at a lower sieve. Then, 2 g of the toner is placed on the upper sieve, the table is vibrated, and a weight (g) of the toner remaining on each sieve is weighed.

The extent of aggregation (%) is calculated by plugging the weight of the toner measured into the following formula.

Extent of Aggregation (%)=$a+b+c$ a=(Weight of Toner Remaining on Upper Sieve)/2×100 b=(Weight of Toner Remaining on Middle Sieve)/2×100×(3/5)

c=(Weight of Toner Remaining on Lower Sieve)/2×100×(1/5)

[Evaluation Criteria of Fluidity]

3: The extent of aggregation is less than 20%.

2: The extent of aggregation is 20% or more and less than 40%.

1: The extent of aggregation is 40% by weight or more.

TABLE II-1

| | Catalyst[1] | Amount [X] (Parts by wt.) | Promoter[2] | Amount [Y] (Parts by wt.) | Y/X | Reaction Time (hr) | Fluidity |
|---|---|---|---|---|---|---|---|
| Comp. Ex. II-1 | S1 | 0.5 | — | — | — | 25.5 | 1 |
| Ex. II-1 | S1 | 0.5 | P1 | 0.05 | 0.10 | 6.5 | 3 |
| Ex. II-2 | S1 | 0.5 | P2 | 0.05 | 0.10 | 7.0 | 3 |
| Ex. II-3 | S1 | 0.5 | P3 | 0.05 | 0.10 | 7.5 | 3 |
| Ex. II-4 | S1 | 0.5 | P4 | 0.05 | 0.10 | 7.5 | 3 |
| Ex. II-5 | S1 | 0.5 | P5 | 0.05 | 0.10 | 10.0 | 2 |
| Ex. II-6 | S1 | 0.5 | P6 | 0.05 | 0.10 | 12.5 | 2 |
| Ex. II-7 | S1 | 0.5 | P7 | 0.05 | 0.10 | 7.5 | 3 |
| Ex. II-8 | S1 | 0.5 | P8 | 0.05 | 0.10 | 13.5 | 2 |
| Ex. II-9 | S1 | 0.5 | P9 | 0.05 | 0.10 | 14.0 | 2 |
| Ex. II-10 | S1 | 0.5 | P10 | 0.05 | 0.10 | 17.5 | 3 |
| Comp. Ex. II-2 | S1 | 0.5 | P11 | 0.05 | 0.10 | 25.5 | 1 |
| Comp. Ex. II-3 | S1 | 0.5 | P12 | 0.05 | 0.10 | 22.5 | 1 |
| Comp. Ex. II-4 | S1 | 0.5 | P13 | 0.05 | 0.10 | 26.0 | 1 |
| Comp. Ex. II-5 | S2 | 0.5 | — | — | — | 29.0 | 1 |
| Ex. II-11 | S2 | 0.5 | P1 | 0.05 | 0.10 | 7.5 | 3 |
| Comp. Ex. II-6 | S3 | 0.5 | — | — | — | 37.0 | 1 |
| Ex. II-12 | S3 | 0.5 | P1 | 0.05 | 0.10 | 18.0 | 2 |
| Comp. Ex. II-7 | S4 | 0.5 | — | — | — | 36.5 | 1 |
| Ex. II-13 | S4 | 0.5 | P1 | 0.05 | 0.10 | 19.5 | 2 |
| Comp. Ex. II-8 | S1 | 0.5 | — | — | — | 25.5 | 1 |
| Ex. II-14 | S1 | 0.5 | P1 | 0.01 | 0.02 | 18.5 | 2 |
| Ex. II-15 | S1 | 0.5 | P1 | 0.10 | 0.20 | 8.5 | 3 |
| Ex. II-16 | S1 | 0.5 | P1 | 0.20 | 0.40 | 18.0 | 2 |
| Comp. Ex. II-9 | S1 | 1.5 | — | — | — | 26.0 | 1 |
| Ex. II-17 | S1 | 1.5 | P1 | 0.40 | 0.27 | 17.5 | 2 |
| Ex. II-18 | S1 | 1.5 | P1 | 1.00 | 0.67 | 20.5 | 2 |
| Comp. Ex. II-10 | S1 | 0.3 | — | — | — | 35.0 | 1 |
| Ex. II-19 | S1 | 0.3 | P1 | 0.05 | 0.17 | 12.5 | 3 |
| Comp. Ex. II-11 | S1 | 0.1 | — | — | — | 50 Hrs or More (Not Completed) | |
| Ex. II-20 | S1 | 0.1 | P1 | 0.01 | 0.10 | 21.5 | 2 |
| Ref. Ex. II-1 | — | — | P1 | 0.05 | — | 50 Hrs or More (Not Completed) | |

Note)
The amount (parts by wt.) of the catalyst and the promoter used is an amount based on 100 parts by weight of the raw material monomers.

[1] S1: Tin(II) 2-ethylhexanoate  S2: Tin(II) stearate  S3: Tin(II) oxide  S4: Tin(II) chloride

[2] P1: Pyrogallic acid  P2: Ethyl pyrogallate  P3: Propyl pyrogallate  P4: Butyl pyrogallate  P5: Octyl pyrogallate  P6: Lauryl pyrogallate  P7: Pyrogallol  P8: 2,3,4-Trihydroxybenzophenone  P9: 2,2',3,4-Tetrahydroxybenzophenone  P10: Epigallocatechin  P11: Phloroglucinol (1,3,5-Trihydroxybenzene)  P12: Ethylene bis(stearamide)  P13: 2-t-Butylhydroquinone

Example II-21 and Comparative Example II-12

A 10-liter four-necked flask equipped with a nitrogen inlet tube, a dehydration tube, a stirrer, and a thermocouple was charged with 4,500 g of 1,4-butanediol, 5,800 g of fumaric acid (100 mol based on 100 mol of 1,4-butanediol), and a catalyst and a promoter shown in Table II-2. The ingredients in the flask were subjected to a polycondensation reaction at 190° C. under a nitrogen gas atmosphere, to give a polyester. The time at a point that the reaction ratio (Amount of Water Formed in Reaction (mol)/Theoretical Amount of Water Formed (mol)×100) reached to 90% was determined. The results are shown in Table II-2. The abbreviations of the catalyst and the promoter are the same as those in Table II-1.

Further, a toner was produced in the same manner as in Example II-1 using the resulting polyester, and fluidity was evaluated. The results are shown in Table II-2.

TABLE II-2

|  | Catalyst[1] | Amount [X] (Parts by wt.) | Promoter[2] | Amount [Y] (Parts by wt.) | Y/X | Reaction Time (hr) | Fluidity |
|---|---|---|---|---|---|---|---|
| Comp. Ex. II-12 | S1 | 0.5 | — | — | — | 18.0 | 1 |
| Ex. II-21 | S1 | 0.5 | P1 | 0.05 | 0.10 | 9.5 | 2 |

Note)
The amount (parts by wt.) of the catalyst and the promoter used is an amount based on 100 parts by weight of the raw material monomers.

Example II-22 and Comparative Example II-13

A 2-liter four-necked flask equipped with a nitrogen inlet tube, a dehydration tube, a stirrer, and a thermocouple was charged with 1,000 g of a 90% by weight aqueous L-lactic acid solution, and a catalyst and a promoter (pyrogallic acid) shown in Table II-3. The ingredients in the flask were subjected to a polycondensation reaction under a nitrogen gas atmosphere while heating so as to raise the temperature from 120° C. to 180° C. at a rate of 5° C./min. Thereafter, the resulting mixture was reacted at 150° C. at 60 Torr for 1 hour, to give a polylactic acid. The molecular weight of the resulting polylactic acid is shown in Table II-3. The abbreviations of the catalyst and the promoter are the same as those in Table II-1.

TABLE II-3

|  | Catalyst[1] | Amount [X] (Parts by wt.) | Promoter[2] | Amount [Y] (Parts by wt.) | Y/X | Molecular Weight |
|---|---|---|---|---|---|---|
| Comp. Ex. II-13 | S1 | 0.5 | — | — | — | 1,150 |
| Ex. II-22 | S1 | 0.5 | P1 | 0.05 | 0.10 | 2,080 |

Note)
The amount (parts by wt.) of the catalyst and the promoter used is an amount based on 100 parts by weight of the raw material monomers.

It can be seen from the above results of the reaction time and the molecular weight that the catalytic activity is increased and the reaction is accelerated because a pyrogallol compound is used as a promoter together with the catalyst in the polycondensation reaction. In other words, in Examples II-1 to II-21, the reaction time necessitated to proceed the reaction to the same level is markedly shortened, as compared to those in the corresponding Comparative Examples. Also, while the molecular weight is increased only to 1,150 in Comparative Example II-13 where only the catalyst is used, the molecular weight is increased to 2,080 even with the same reaction time in Example II-22 where pyrogallol compound is used together. In addition, it can be seen that the resins obtained in Examples II-1 to II-21 exhibit excellent fluidity also as resin binders for a toner.

Examples III-1 to III-17, Comparative Examples III-1 to III-7, and Reference Example III-1

A 10-liter four-necked flask equipped with a nitrogen inlet tube, a dehydration tube, a stirrer, and a thermocouple was charged with 6,520 g of polyoxypropylene(2.0)-2,2-bis(4-hydroxyphenyl)propane (BPA-PO), 3,320 g of terephthalic acid (100 mol based on 100 mol of BPA-PO), and a catalyst and a promoter shown in Table III-1. The ingredients in the flask were reacted at 235° C. under a nitrogen gas atmosphere, and the reaction ratio (Amount of Water Formed in Reaction (mol)/Theoretical Amount of Water Formed (mol)×100) was calculated from the amount of water in the reaction at each passage of time. Here, the resulting resins are grouped into A to F by the kinds of the catalyst and the promoter and the like and shown together with the properties in Table III-1.

TABLE III-1

| Group | | Catalyst[1] | Amount [X] (Parts by wt.) | Promoter[2] | Amount [Y] (Parts by wt.) | Y/X | Reaction Ratio (%) at Each Reaction Time (hr) | | | |
|---|---|---|---|---|---|---|---|---|---|---|
| | | | | | | | 0.5 hr | 1.5 hr | 3 hr | 5 hr |
| A | Comp. Ex. III-1 | T1 | 0.5 | — | — | — | 27 | 42 | 45 | 46 |
| | Ex. III-1 | T1 | 0.5 | P1 | 0.05 | 0.10 | 30 | 57 | 71 | 78 |
| | Ex. III-2 | T1 | 0.5 | P2 | 0.05 | 0.10 | 28 | 56 | 72 | 76 |
| | Ex. III-3 | T1 | 0.5 | P3 | 0.05 | 0.10 | 27 | 53 | 69 | 74 |
| | Ex. III-4 | T1 | 0.5 | P4 | 0.05 | 0.10 | 27 | 47 | 51 | 56 |
| | Ex. III-5 | T1 | 0.5 | P5 | 0.05 | 0.10 | 27 | 45 | 50 | 53 |
| | Ex. III-6 | T1 | 0.5 | P6 | 0.05 | 0.10 | 29 | 59 | 70 | 76 |
| | Ex. III-7 | T1 | 0.5 | P7 | 0.05 | 0.10 | 27 | 49 | 56 | 61 |
| | Ex. III-8 | T1 | 0.5 | P8 | 0.05 | 0.10 | 27 | 47 | 55 | 62 |
| | Ex. III-9 | T1 | 0.5 | P9 | 0.05 | 0.10 | 27 | 45 | 53 | 58 |
| | Comp. Ex. III-2 | T1 | 0.5 | P10 | 0.05 | 0.10 | 27 | 40 | 43 | 44 |
| B | Comp. Ex. III-3 | T2 | 0.5 | — | — | — | 22 | 37 | 42 | 44 |
| | Ex. III-10 | T2 | 0.5 | P1 | 0.05 | 0.10 | 23 | 53 | 65 | 72 |
| C | Comp. Ex. III-4 | T3 | 0.5 | — | — | — | 24 | 39 | 44 | 45 |
| | Ex. III-11 | T3 | 0.5 | P1 | 0.05 | 0.10 | 26 | 57 | 67 | 73 |
| D | Comp. Ex. III-5 | T1 | 0.5 | — | — | — | 27 | 42 | 45 | 46 |
| | Ex. III-12 | T1 | 0.5 | P1 | 0.01 | 0.02 | 28 | 54 | 66 | 71 |
| | Ex. III-13 | T1 | 0.5 | P1 | 0.10 | 0.20 | 26 | 53 | 64 | 68 |
| | Ex. III-14 | T1 | 0.5 | P1 | 0.20 | 0.40 | 25 | 49 | 53 | 56 |
| E | Comp. Ex. III-6 | T1 | 1.5 | — | — | — | 28 | 43 | 46 | 46 |
| | Ex. III-15 | T1 | 1.5 | P1 | 0.40 | 0.27 | 28 | 56 | 64 | 67 |
| | Ex. III-16 | T1 | 1.5 | P1 | 1.00 | 0.67 | 24 | 48 | 52 | 55 |
| F | Comp. Ex. III-7 | T1 | 0.1 | — | — | — | 17 | 31 | 34 | 36 |
| | Ex. III-17 | T1 | 0.1 | P1 | 0.01 | 0.10 | 18 | 42 | 46 | 51 |
| | Ref. Ex. III-1 | — | — | P1 | 0.05 | — | 0 | 0 | 0 | 0 |

Note)
The amount (parts by wt.) of the catalyst and the promoter used is an amount based on 100 parts by weight of the raw material monomers.
[1] T1: Titanium diisopropylate bis(triethanolaminate) T2: Titanium diisopropylate bis(diethanolaminate) T3: Titanium diisopentylate bis(triethanolaminate)
[2] P1: Pyrogallic acid P2: Ethyl pyrogallate P3: Butyl pyrogallate P4: Octyl pyrogallate P5: Lauryl pyrogallate P6: Pyrogallol P7: 2,3,4-Trihydroxybenzophenone P8: 2,2',3,4-Tetrahydroxybenzophenone P9: Epigallocatechin P10: Phloroglucinol (1,3,5-Trihydroxybenzene)

Example III-18 and Comparative Example III-8

A 10-liter four-necked flask equipped with a nitrogen inlet tube, a dehydration tube, a stirrer, and a thermocouple was charged with 4,500 g of 1,4-butanediol, 5,800 g of fumaric acid (100 mol based on 100 mol of 1,4-butanediol), and a catalyst and a promoter shown in Table III-2. The ingredients in the flask were subjected to a polycondensation reaction at 190° C. under a nitrogen gas atmosphere, to give a polyester. The acid value reached to 35 mgKOH/g, and thereafter the resulting polyester was subjected to a vacuum reaction at 8 kPa. A part of the reaction mixture was collected every 0.5 hours and the acid value was determined, to obtain the time to reach to an acid value of 5 mgKOH/g. The results are shown in Table III-2. The abbreviations of the catalyst, the promoter, and the group are the same as those in Table III-1.

TABLE III-2

| Group | | Catalyst[1] | Amount [X] (Parts by wt.) | Promoter[2] | Amount [Y] (Parts by wt.) | Y/X | Reaction Time (hr) |
|---|---|---|---|---|---|---|---|
| G | Comp. Ex. III-8 | T1 | 0.5 | — | — | — | 9.5 |
|   | Ex. III-18 | T1 | 0.5 | P1 | 0.05 | 0.10 | 2.5 |

Note)
The amount (parts by wt.) of the catalyst and the promoter used is an amount based on 100 parts by weight of the raw material monomers.

Examples III-19 to III-25 and Comparative Examples III-9 to III-11

A 10-liter four-necked flask equipped with a nitrogen inlet tube, a dehydration tube, a stirrer, and a thermocouple was charged with 5,420 g of polyoxypropylene(2.2)-2,2-bis(4-hydroxyphenyl)propane (BPA-PO) (80 mol), 1,227 g of polyoxyethylene(2.2)-2,2-bis(4-hydroxyphenyl)propane (BPA-EO) (20 mol), 2,324 g of terephthalic acid (70 mol based on 100 mol of the total amount of BPA-PO and BPA-EO), and a catalyst and a promoter shown in Table III-3. The ingredients in the flask were reacted at 235° C. under a nitrogen gas atmosphere until the reaction ratio (Amount of Water Formed in Reaction (mol)/Theoretical Amount of Water Formed (mol)×100) reached to 95%. Thereafter, 768 g of trimellitic acid (TMA) (20 mol based on 100 mol of the total amount of BPA-PO and BPA-EO) was added thereto and the mixture was reacted at 210° C. until the softening point reached to 115° C., to give a polyester. The results are shown in Table III-3. The abbreviations of the catalyst, the promoter, and the group are the same as those in Table III-1.

One-hundred parts by weight of the resulting polyester, 4 parts by weight of a carbon black "MOGUL L" (commercially available from Cabot Corporation), 1 part by weight of a negative charge control agent "T-77" (commercially available from Hodogaya Chemical Co., Ltd), and 1 part by weight of a polypropylene wax "NP-105" (commercially available from MITSUI CHEMICALS, INC., melting point of 140° C.) were sufficiently mixed with a Henschel mixer. Thereafter, the mixture was melt-kneaded with a co-rotating twin-screw extruder having an entire length of the kneading portion of 1560 mm, a screw diameter of 42 mm and a barrel inner diameter of 43 mm at a rotational speed of the roller of 200 r/min, and a heating temperature within the roller of 80° C. The feeding rate of the mixture was 20 kg/hr, and the average residence time was about 18 seconds. The resulting melt-kneaded product was cooled and roughly pulverized, and thereafter pulverized with a jet mill and classified, to give a powder having a volume-median particle size ($D_{50}$) of 8.0 μm.

The amount 0.1 parts by weight of a hydrophobic silica "Aerosil R-972" (commercially available from Nippon Aerosil) was added as an external additive to 100 parts by weight of the resulting powder, and the mixture was mixed with a Henschel mixer, to give a toner.

Three parts by weight of an iron powder carrier "FL93-100" (commercially available from Powdertech Co., Ltd., volume-average particle size: 100 μm) was mixed with 97 parts by weight of the resulting toner, and the mixture was blended with a ball mill for 10 minutes. Thereafter, the triboelectric charge was determined. The results are shown in Table III-3.

TABLE III-3

| Group | | Catalyst[1] | Amount [X] (Parts by wt.) | Promoter[2] | Amount [Y] (Parts by wt.) | Y/X | Reaction Time Until Reaction Ratio Reached to 95% (hr) | Reaction Time After Addition of TMA (hr) | Triboelectric Chargeability of Toner (μC/g) |
|---|---|---|---|---|---|---|---|---|---|
| H | Comp. Ex. III-9 | T1 | 0.5 | — | — | — | 13.0 | 6.0 | −21.3 |
|   | Ex. III-19 | T1 | 0.5 | P1 | 0.05 | 0.10 | 3.0 | 3.0 | −33.7 |
|   | Ex. III-20 | T1 | 0.5 | P2 | 0.05 | 0.10 | 3.5 | 3.0 | −32.2 |
|   | Ex. III-21 | T1 | 0.5 | P3 | 0.05 | 0.10 | 3.5 | 3.5 | −31.5 |
|   | Ex. III-22 | T1 | 0.5 | P6 | 0.05 | 0.10 | 3.0 | 3.5 | −32.9 |
|   | Ex. III-23 | T1 | 0.5 | P7 | 0.05 | 0.10 | 5.0 | 4.0 | −29.7 |
| I | Comp. Ex. III-10 | T2 | 0.5 | — | — | — | 14.5 | 7.5 | −19.5 |
|   | Ex. III-24 | T2 | 0.5 | P1 | 0.05 | 0.10 | 4.0 | 3.5 | −32.0 |
| J | Comp. Ex. III-11 | T3 | 0.5 | — | — | — | 14.0 | 7.0 | −20.3 |
|   | Ex. III-25 | T3 | 0.5 | P1 | 0.05 | 0.10 | 4.5 | 4.0 | −31.8 |

Note)
The amount (parts by wt.) of the catalyst and the promoter used is an amount based on 100 parts by weight of the raw material monomers.

It can be seen from the above monitoring of the reaction ratio and the above results of the reaction time that the catalytic activity is increased and the reaction is accelerated because a pyrogallol compound is used as a promoter together with the catalyst in the polycondensation reaction. In other words, in Examples III-1 to III-17, prevention of the deactivation of the catalytic activity has been confirmed, as compared to each of Comparative Examples in the same groups. The prevention of the deactivation of the catalytic activity could be also confirmed from the comparison between Example III-18 and Comparative Example III-8 which have been previously polycondensed with the another monomer composition. Further, in Examples III-19 to III-25, the reaction time necessitated to proceed the reaction to the same level is markedly shortened, as compared to those in each of Comparative Examples in the same group. In addition, it can be seen that the resins obtained in Examples III-19 to III-25 have a sufficiently high triboelectric charge and exhibit an excellent triboelectric chargeability also as resin binders for a toner.

Examples IV-1 to IV-18, Comparative Examples IV-1 to IV-7, and Reference Examples IV-1 and IV-2

Production Example IV-1 for Resin

A 10-liter four-necked flask equipped with a nitrogen inlet tube, a dehydration tube, a stirrer, and a thermocouple was charged with 3,318 g of polyoxypropylene(2.1)-2,2-bis(4-hydroxyphenyl)propane (BPA-PO) (50 mol), 3,024 g of polyoxyethylene(2.1)-2,2-bis(4-hydroxyphenyl)propane (BPA-EO) (50 mol), 2,988 g of terephthalic acid (90 mol based on 100 mol of the total amount of BPA-PO and BPA-EO), and a catalyst and a promoter shown in Table IV-1. The ingredients in the flask were reacted at 235° C. under a nitrogen gas atmosphere until the reaction ratio (Amount of Water Formed in Reaction (mol)/Theoretical Amount of Water Formed (mol)×100) reached to 93%. Thereafter, the mixture was reacted at 8 kPa until the softening point reached to 100° C., to give a polyester.

Production Example IV-1 for Toner

One-hundred parts by weight of the polyester obtained in Production Example IV-1 for Resin, 4 parts by weight of a yellow pigment "Paliotol Yellow D1155" (C.I. Pigment Yellow 185, commercially available from BASF Corporation), 1 part by weight of a negative charge control agent "BONTRON E-84" (commercially available from Orient Chemical Co., Ltd.), and 3 parts by weight of a carnauba wax "Carnauba Wax C1" (commercially available from Kato Yoko, melting point of 83° C.) were sufficiently mixed with a Henschel mixer. Thereafter, the mixture was melt-kneaded with a co-rotating twin-screw extruder having an entire length of the kneading portion of 1560 mm, a screw diameter of 42 mm and a barrel inner diameter of 43 mm at a rotational speed of the roller of 200 r/min, and a heating temperature within the roller of 80° C. The feeding rate of the mixture was 20 kg/hr, and the average residence time was about 18 seconds. The resulting melt-kneaded product was cooled and roughly pulverized, and thereafter pulverized with a jet mill and classified, to give a powder having a volume-median particle size ($D_{50}$) of 8.0 μm.

One part by weight of a hydrophobic silica "Aerosil R-972" (commercially available from Nippon Aerosil) was added as an external additive to 100 parts by weight of the resulting powder, and the mixture was mixed with a Henschel mixer, to give a toner. Here, the resulting toners are grouped into A to F by the kinds of the catalyst and the promoter and the like and shown together with the properties in Table IV-1.

Test Example IV-1

The toner was loaded in a nonmagnetic monocomponent development device "Oki Microline 5400" (commercially available from Oki Data Corporation), and images of a diagonally striped pattern with a printing ratio of 5.5% were printed out for 50 sheets. After printing, a solid image with an image density of 1.3, having a size of 5 cm×5 cm, was printed out, and L* value, a* value, and b* value were determined using a color-difference meter "CR-321" (commercially available from KONICA MINOLTA HOLDINGS, INC.). The L* value, a* value, and b* value of the solid image obtained by carrying out the similar printing test using the toner of Reference Example IV-2 were defined as the standard values. ΔE was calculated according to the following formula:

$$\Delta E = \sqrt{(L_1^* - L_2^*)^2 + (a_1^* - a_2^*)^2 + (b_1^* - b_2^*)^2}$$

wherein each of $L_1^*$, $a_1^*$ and $b_1^*$ is a value determined, and each of $L_2^*$, $a_2^*$ and $b_2^*$ is a value determined for the toner in Reference Example IV-2, to evaluate as coloring property. The results are shown in Table IV-1.

Test Example IV-2

The toner was loaded in a nonmagnetic monocomponent development device "Oki Microline 5400" (commercially available from Oki Data Corporation), and images of a diagonally striped pattern with a printing ratio of 5.5% were printed out for 50 sheets. After printing, a white solid image (printing ratio: 0%) was printed out, and each of the average values of L* value, a* value, and b* value was calculated for any 4 points in the same manner as in Test Example IV-1. Setting the L* value, a* value, and b* value of a blank sheet as the standards, ΔE was calculated in the same manner as in Test Example IV-1, to evaluate as the background fog. The results are shown in Table IV-1.

TABLE IV-1

| Group | | Catalyst[1] | Amount [X] (Parts by wt.) | Promoter[2] | Amount [Y] (Parts by wt.) | Y/X | Reaction Time (hr) | Coloring Property ΔE | Background Fog ΔE |
|---|---|---|---|---|---|---|---|---|---|
| A | Comp. Ex. IV-1 | T1 | 0.5 | — | — | — | 29.0 | 8.2 | 4.3 |
| | Ex. IV-1 | T1 | 0.5 | P1 | 0.05 | 0.10 | 13.0 | 1.0 | 0.3 |
| | Ex. IV-2 | T1 | 0.5 | P1 | 0.01 | 0.02 | 22.0 | 6.8 | 3.1 |
| | Ex. IV-3 | T1 | 0.5 | P1 | 0.10 | 0.20 | 14.5 | 1.9 | 0.4 |
| | Ex. IV-4 | T1 | 0.5 | P1 | 0.20 | 0.40 | 19.0 | 2.4 | 0.7 |
| | Ex. IV-5 | T1 | 0.5 | P2 | 0.05 | 0.10 | 13.5 | 0.7 | 0.2 |
| | Ex. IV-6 | T1 | 0.5 | P3 | 0.05 | 0.10 | 14.0 | 0.8 | 0.3 |
| | Ex. IV-7 | T1 | 0.5 | P4 | 0.05 | 0.10 | 17.0 | 2.5 | 0.9 |
| | Ex. IV-8 | T1 | 0.5 | P5 | 0.05 | 0.10 | 18.5 | 3.1 | 1.3 |
| | Ex. IV-9 | T1 | 0.5 | P6 | 0.05 | 0.10 | 12.0 | 4.9 | 0.4 |
| | Ex. IV-10 | T1 | 0.5 | P7 | 0.05 | 0.10 | 18.0 | 6.3 | 1.1 |
| | Ex. IV-11 | T1 | 0.5 | P8 | 0.05 | 0.10 | 19.0 | 6.1 | 1.2 |
| | Ex. IV-12 | T1 | 0.5 | P9 | 0.05 | 0.10 | 21.5 | 6.4 | 1.4 |
| | Comp. Ex. IV-2 | T1 | 0.5 | P10 | 0.05 | 0.10 | 28.5 | 9.6 | 4.7 |

TABLE IV-1-continued

| Group | | Catalyst[1] | Amount [X] (Parts by wt.) | Promoter[2] | Amount [Y] (Parts by wt.) | Y/X | Reaction Time (hr) | Coloring Property ΔE | Background Fog ΔE |
|---|---|---|---|---|---|---|---|---|---|
| B | Comp. Ex. IV-3 | T2 | 0.5 | — | — | — | 32.5 | 8.9 | 4.7 |
| | Ex. IV-13 | T2 | 0.5 | P1 | 0.05 | 0.10 | 15.5 | 2.0 | 0.9 |
| C | Comp. Ex. IV-4 | T3 | 0.5 | — | — | — | 40.0 | 9.5 | 5.6 |
| | Ex. IV-14 | T3 | 0.5 | P1 | 0.05 | 0.10 | 18.0 | 3.7 | 1.9 |
| D | Comp. Ex. IV-5 | T4 | 0.5 | — | — | — | 42.5 | 9.8 | 5.4 |
| | Ex. IV-15 | T4 | 0.5 | P1 | 0.05 | 0.10 | 19.0 | 4.1 | 1.7 |
| E | Comp. Ex. IV-6 | T1 | 1.5 | — | — | — | 30.5 | 9.6 | 5.3 |
| | Ex. IV-16 | T1 | 1.5 | P1 | 0.40 | 0.27 | 16.5 | 2.0 | 0.5 |
| | Ex. IV-17 | T1 | 1.5 | P1 | 1.00 | 0.67 | 19.5 | 2.6 | 1.1 |
| F | Comp. Ex. IV-7 | T1 | 0.1 | — | — | — | Reaction Time of 50 Hr or More (Not Completed) | | |
| | Ex. IV-18 | T1 | 0.1 | P1 | 0.01 | 0.10 | 27.0 | 7.1 | 2.8 |
| | Ref. Ex. IV-1 | — | — | P1 | 0.05 | — | Reaction Time of 50 Hr or More (Not Completed) | | |
| | Ref. Ex. IV-2 | S1 | 0.2 | — | — | — | 10.0 | 0 (Standard Value) | 0.8 |

Note)
The amount (parts by wt.) of the catalyst and the promoter used is an amount based on 100 parts by weight of the raw material monomers.
[1]T1: Tetrastearyl titanate T2: Dioctyldihydroxyoctyl titanate T3: Tetrabutyl titanate T4: Tetrapropyl titanate S1: Dibutyltin oxide
[2]P1: Pyrogallic acid P2: Ethyl pyrogallate P3: Butyl pyrogallate P4: Octyl pyrogallate P5: Lauryl pyrogallate P6: Pyrogallol P7: 2,3,4-Trihydroxybenzophenone P8: 2,2',3,4-Tetrahydroxybenzophenone P9: Epigallocatechin P10: Phloroglucinol (1,3,5-Trihydroxybenzene)

Example IV-19 and Comparative Example IV-8

Production Example IV-2 for Resin

A 10-liter four-necked flask equipped with a nitrogen inlet tube, a dehydration tube, a stirrer, and a thermocouple was charged with 4,500 g of 1,4-butanediol, 5,800 g of fumaric acid (100 mol based on 100 mol of 1,4-butanediol), and a catalyst and a promoter shown in Table IV-2. The ingredients in the flask were reacted at 190° C. under a nitrogen gas atmosphere until the reaction ratio (Amount of Water Formed in Reaction (mol)/Theoretical Amount of Water Formed (mol)×100) reached to 93%, to give a polyester. The results are shown in Table IV-2. The abbreviations of the catalyst, the promoter, and the group are the same as those in Table IV-1.

Production Example IV-2 for Toner

The same procedures as in Production Example IV-1 for Toner were carried out except that 100 parts by weight of the polyester obtained in Production Example IV-2 for Resin was used in place of 100 parts by weight of the polyester resin obtained in Production Example IV-1 for Resin, to produce a toner. Coloring property and the background fog were evaluated. The results are shown in Table IV-2.

It can be seen from the above results of the reaction time that the catalytic activity is increased and the reaction is accelerated because a pyrogallol compound is used as a promoter together with the catalyst in the polycondensation reaction. In other words, in Examples IV-1 to IV-19, the reaction time necessitated to proceed the reaction to the same level is markedly shortened, as compared to each of Comparative Examples in the same group. In addition, it can be seen that the resins obtained in Examples have a low degree of coloration and are efficient in prevention of the background fog also as resin binders for a toner.

Production Examples V-1 to V-8 for Resin

A 10-liter four-necked flask equipped with a nitrogen inlet tube, a dehydration tube, a stirrer, and a thermocouple was charged with 5,145 g of polyoxypropylene(2.2)-2,2-bis(4-hydroxyphenyl)propane, 2,048 g of polyoxyethylene(2.2)-2,2-bis(4-hydroxyphenyl)propane, 2,092 g of terephthalic acid, and a catalyst and a pyrogallol compound shown in Table V-1. The ingredients in the flask were subjected to a polycondensation reaction at 235° C. under a nitrogen gas atmosphere until the acid value reached to 10 mgKOH/g. Thereafter, the temperature was lowered to 180° C., and 901 g of fumaric acid and 5 g of hydroquinone were added thereto. The mixture

TABLE IV-2

| Group | | Catalyst[1] | Amount [X] (Parts by wt.) | Promoter[2] | Amount [Y] (Parts by wt.) | Y/X | Reaction Time (hr) | Coloring Property ΔE | Background Fog ΔE |
|---|---|---|---|---|---|---|---|---|---|
| G | Comp. Ex. IV-8 | T1 | 0.5 | — | — | — | 23.0 | 6.8 | 6.3 |
| | Ex. IV-19 | T1 | 0.5 | P1 | 0.05 | 0.10 | 14.5 | 1.6 | 2.4 |

Note)
The amount (parts by wt.) of the catalyst and the promoter used is an amount based on 100 parts by weight of the raw material monomers.

was reacted while raising the temperature from 180° C. to 210° C. for 3 hours, and the temperature reached to 210° C. Thereafter, the reaction mixture was further reacted at 8 kPa, to give resins A to H. Here, all of the resins had a softening point of 105° C. and a glass transition temperature of 61° C.

TABLE V-1

| Catalyst | Pyrogallol Compound | Pyrogallol Compound/ Catalyst |
|---|---|---|---|
| Resin A | Tin(II) 2-Ethylhexanoate/0.5 | — | — |
| Resin B | Tin(II) 2-Ethylhexanoate/0.5 | Pyrogallic Acid/0.05 | 0.1 |
| Resin C | Tin(II) 2-Ethylhexanoate/0.5 | Pyrogallic Acid/0.02 | 0.04 |
| Resin D | Tin(II) 2-Ethylhexanoate/0.5 | Pyrogallic Acid/0.1 | 0.2 |
| Resin E | Tin(II) 2-Ethylhexanoate/0.5 | Pyrogallic Acid/0.02 | 0.067 |
| Resin F | Tin(II) 2-Ethylhexanoate/0.5 | Pyrogallol/0.05 | 0.1 |
| Resin G | Tin(II) 2-Ethylhexanoate/0.5 | Pyrogallic Acid/0.01 | 0.005 |
| Resin H | Tin(II) 2-Ethylhexanoate/0.5 | Pyrogallic Acid/1.0 | 0.5 |

Note)
The amount (parts by wt.) of the catalyst and the pyrogallol compound used is an amount based on 100 parts by weight of the total amount of the raw material monomers.

Examples V-A1 to V-A7 and Comparative Example V-A1

A 5-liter vessel equipped with a stirrer, a reflux condenser, a dropping funnel, a thermometer, and a nitrogen inlet tube was charged with 600 g of methyl ethyl ketone, and 200 g of a resin shown in Table V-2 was added thereto at room temperature to dissolve. Ten grams of triethylamine was added to the resulting solution to neutralize the solution, and subsequently 2,000 g of ion-exchanged water was added thereto. Thereafter, methyl ethyl ketone was distilled away from the mixture under a reduced pressure at a temperature of 50° C. or lower at a stirring rate of 250 r/min, to give a resin dispersion prepared by dispersing self-dispersible water-based resin particles (resin content: 9.6% by weight (calculated as solid content)). The resin particles dispersed in the resulting resin dispersion had a volume-average particle size ($D_4$) of 0.096 μm.

Fifty grams of copper phthalocyanine (commercially available from DAINICHISEIKA COLOR & CHEMICALS MFG. CO., LTD.), 5 g of a nonionic surfactant (EMULGEN 150, commercially available from KAO Corporation), and 200 g of ion-exchanged water were mixed, to dissolve copper phthalocyanine. The liquid mixture was dispersed using a homogenizer for 10 minutes, to give a dispersed coloring agent dispersion.

Fifty grams of a paraffin wax (HNP0190, commercially available from Nippon Seiro, melting point: 85° C.), 5 g of a cationic surfactant (SANISOL B50, commercially available from KAO Corporation), and 200 g of ion-exchanged water were heated to 95° C., and the paraffin wax was dispersed using a homogenizer. Thereafter, the resulting dispersion was subjected to a dispersion treatment with a pressure injection homogenizer, to give a releasing agent dispersion in which the paraffin wax having an average particle size of 550 nm was dispersed.

Fifty grams of a charge control agent (BONTRON E-84, commercially available from Orient Chemical Co., Ltd.), 5 g of a nonionic surfactant (EMULGEN 150, commercially available from KAO Corporation), and 200 g of ion-exchanged water were mixed. The charge control agent was dispersed with a sand grinder for 10 minutes using glass beads, to prepare a charge control agent dispersion in which the charge control agent having an average particle size of 500 nm was dispersed. Remnants of coarse particles were observed in the dispersion.

Four-hundred and ninety grams of the resulting resin particles dispersion, 20 g of the coloring agent dispersion, 15 g of the releasing agent dispersion, 7 g of the charge control agent dispersion, and 2 g of a cationic surfactant (SANISOL B50, commercially available from KAO Corporation) were mixed in a round stainless-steel flask using a homogenizer, to disperse. Thereafter, the flask was heated to 48° C. in an oil bath for heating while stirring the mixture in the flask. Further, the flask was maintained at 48° C. for 1 hour, and it was then confirmed that aggregate particles having a volume-median particle size ($D_{50}$) of 7.0 μm were formed.

Three grams of an anionic surfactant (PELEX SS-L, commercially available from KAO Corporation) was added to the aggregate particles dispersion in which the aggregate particles were formed. Thereafter, a reflux tube was attached to the above-mentioned stainless-steel flask, and the mixture was heated to 80° C. at a rate of 5° C./min while continuously stirring, and maintained for 5 hours, to unify the aggregate particles and fuse together. Subsequently, the mixture was cooled, and the fused particles were filtered, sufficiently washed with ion-exchanged water, and then dried. The fine colored resin particle powder thus obtained had a volume-median particle ($D_{50}$) of 7.1 μm.

The amount 1.0 part by weight of a hydrophobic silica (TS530, commercially available from Wacker Chemicals, number-average particle size: 8 nm) was added to 100 parts by weight of the resulting fine colored resin particle powder, and externally added by blending the mixture with a Henschel mixer, to give a cyan toner. The resulting cyan toner had a volume-median particle size ($D_{50}$) of 7.1 μm.

Incidentally, in Comparative Example V-A1, deposition of white precipitates was found in the resin dispersion.

Example V-B1 and Comparative Example V-B1

Two-hundred grams of a resin shown in Table V-2 and 100 g of a nonionic surfactant (polyoxyethylene lauryl ether (EO=9 mol added), cloud point: 98° C., HLB: 15.3) were melted at 170° C. in a 5-liter stainless-steel vessel, while stirring with a paddle-shaped stirrer at a rate of 200 r/min. The ingredients in the vessel were stabilized at 95° C., which was a temperature 3° C. lower than the cloud point of the nonionic surfactant, and 75.5 g of an aqueous sodium hydroxide solution (concentration: 5% by weight) was added dropwise thereto as a neutralizing agent, while stirring with a paddle-shaped stirrer at a rate of 200 r/min. Subsequently, deionized water was added dropwise to the mixture at a rate of 6 g/min while stirring with the paddle-shaped stirrer at a rate of 300 r/min, totaling to an amount of 1624.5 g. During the addition, the temperature of the system was kept at 95° C., and a resin dispersion in which emulsified particles of the resin were dispersed (resin emulsion) was obtained through a wire mesh having a 200 mesh (sieve opening: 105 μm). The emulsified particles in the resulting resin dispersion (resin particles) had a volume-average particle size ($D_4$) of 0.135 μm and a solid content of 12.0% by weight. No resin components remained on the wire mesh.

Four-hundred grams of the resulting resin dispersion (concentration: 12.3% by weight), 40 g of a cyan pigment-containing aqueous dispersion (concentration: 5% by weight), and 7 g of a paraffin wax (HNP-9, commercially available from Nippon Seiro, melting point: 78° C.)-containing aqueous dispersion (concentration: 35% by weight, nonionic surfactant: 5% by weight of EMULGEN 108 (commercially available from Kao Corporation), dispersion diameter (volume-median particle size) of wax: 0.30 μm) were mixed in a 1-liter vessel at room temperature.

Next, an aqueous solution containing a 1 g portion of calcium chloride as an aggregating agent was added to this mixture and the pH was adjusted to 7.0 with an aqueous sodium carbonate solution (concentration: 10% by weight). Thereafter, the mixture was stirred with a HOMO MIXER at a rotational speed of 5000 r/min at room temperature for 1 hour. The resulting mixed dispersion was transferred to a 1-liter autoclave, heated to 90° C., and stirred at a rate of 500 r/min for 6 hours, to form aggregate particles.

Thereafter, the mixed dispersion was heated to 100° C., and stirred for an additional 1 hour to unify aggregate particles. Subsequently, the mixed dispersion was subjected to a suction filtration step, a washing step, and a drying step, to give a fine colored resin particle powder. The fine colored resin particle powder had a volume-median particle size ($D_{50}$) of 6.9 μm and a water content of 0.3% by weight.

The amount 1.0 part by weight of a hydrophobic silica (TS530, commercially available from Wacker Chemicals, number-average particle size: 8 nm) was added to 100 parts by weight of the resulting fine colored resin particle powder, and externally added by mixing the mixture with a Henschel mixer, to give a cyan toner. The resulting cyan toner had a volume-median particle size ($D_{50}$) of 6.9 μm.

Test Example V-1

Transfer Efficiency

A toner was loaded in a color printer "MICROLINE 5400" (commercially available from Oki Data Corporation) and a solid image was printed out. The amount of toner on the photoconductor of the solid image was adjusted to 0.40 to 0.50 mg/cm$^2$, and the machine was stopped in the course of printing of the solid image. A mending tape was adhered to a photoconductor which passed through a transfer member, so that a toner remaining on the photoconductor without being transferred is transferred to the mending tape, and the mending tape was peeled off from the photoconductor. The peeled mending tape and an unused mending tape were adhered to a blank sheet, and hues of the mending tapes adhered to a blank sheet were determined with a colorimeter "X-Rite" (commercially available from X-Rite), and the transfer efficiency was evaluated on the basis of the difference in hues (ΔE). The transfer efficiency is excellent when ΔE is 4.0 or less. The results are shown in Table V-2.

TABLE V-2

| | Resin | Particle Size of Resin Particles | CV Value of Resin Particles | Transfer Efficiency |
|---|---|---|---|---|
| Ex. V-A1 | Resin B | 96 nm | 22 | 0.4 |
| Ex. V-A2 | Resin C | 152 nm | 29 | 1.3 |
| Ex. V-A3 | Resin D | 125 nm | 24 | 1.2 |
| Ex. V-A4 | Resin E | 100 nm | 23 | 1.0 |
| Ex. V-A5 | Resin F | 105 nm | 21 | 0.9 |
| Ex. V-A6 | Resin G | 210 nm | 63 | 3.0 |
| Ex. V-A7 | Resin H | 190 nm | 45 | 3.6 |
| Comp. Ex. V-A1 | Resin A | 350 nm | 122 | 4.5 |
| Ex. V-B1 | Resin B | 135 nm | 26 | 1.5 |
| Comp. Ex. V-B1 | Resin A | 416 nm | 164 | 4.8 |

It can be seen from the above results that the toners of Examples prepared from a polyester obtained by using a pyrogallol compound as a promoter have resin particles having a small particle size and a sharp particle size distribution, and are excellent in transfer efficiency, as compared to the toners of Comparative Examples. In addition, the polyester obtained by using a pyrogallol compound as a promoter is used, whereby an excellent resin dispersion is obtained without deposition of precipitates even by the method of Example V-B1 where an organic solvent is used.

Example VI-1

First-Step Reaction

A 10-liter four-necked flask equipped with a nitrogen inlet tube, a dehydration tube, a stirrer, and a thermocouple was charged with the raw material monomers in raw material monomer composition A shown in Table VI-1 other than trimellitic acid, and a catalyst and a promoter shown in Table VI-2. The ingredients in the flask were subjected to a polycondensation reaction at 235° C. under a nitrogen gas atmosphere until the reaction ratio reached to 90%. Thereafter, the reaction mixture was further reacted at 8 kPa for 1 hour. The reaction ratio in the first-step reaction was 95%.

Subsequently, a phosphorus-containing compound shown in Table VI-2 was continuously added to the reaction mixture over 5 minutes, and the mixture was stirred for 30 minutes.

[Second-Step Reaction]

Thereafter, trimellitic acid was added to the resulting mixture at 220° C., and the mixture was reacted for 1 hour. Thereafter, the reaction mixture was subjected to a vacuum cross-linking reaction at 8 kPa until a desired softening point was reached. The entire reaction ratio at the termination of the second-step reaction was 91%.

[After Termination of Entire Reaction]

The pressure in the flask was changed back to normal pressure, the heating and stirring were stopped to terminate the reaction, and the resulting resin was drawn out from the flask at a rate of 150 g/min. The draw-out took a time period of about 60 minutes. In order to monitor the change in the softening point of the resin during the draw-out, 100 g of the resin was collected from the flask at the initiation of the draw-out (immediately after the termination of the reaction) and 30 minutes after the initiation of the draw-out. The collected resin was cooled and the softening point was determined, and the difference between the softening points (ΔTm) was obtained. The smaller the ΔTm, the narrower distribution of the molecular weight (distribution of the softening point) the polycondensed resin. The results are shown in Table VI-2.

[Confirmation of State of Reaction when 5% by Weight of Resin Remains in Reaction System]

In order to confirm the influence of remnants on the reaction system on the next batch, accompanied by the batch production of resin, a four-necked flask without a remnant of the resin was charged with totally 9,625 g of polyoxypropylene(2.05)-2,2-bis(4-hydroxyphenyl)propane (BPA-PO), polyoxyethylene(2.05)-2,2-bis(4-hydroxyphenyl)propane (BPA-EO) (BPA-PO/BPA-EO/TPA=85/15/58 (molar ratio)), and terephthalic acid (TPA), together with 500 g (5 parts by weight based on 100 parts by weight of the total amount of BPA-PO, BPA-EO and TPA) of the resin obtained in Example VI-1. The time period up to a point where the acid value reached to 15 mgKOH/g at 235° C. under a nitrogen gas atmosphere was determined and the difference from the reaction time in the ordinary conditions (6.5 hrs) was obtained.

Examples VI-2 to VI-6, VI-8, and VI-9, and Comparative Examples VI-1 to VI-3

The same procedures as in Example VI-1 were carried out except that a catalyst, a promoter and a phosphorus-containing compound, shown in Table VI-2 were used, and the phosphorus-containing compound was added at a point shown in Table VI-2, to give a resin. The change in the softening point was determined, and the same procedures were further carried out with a next batch. The results are shown in Table IV-2.

Example VI-7

The same procedures as in Example VI-1 were carried out except that, in the first-step reaction, the phosphorus-containing compound was continuously added stepwise to the reaction mixture for 5 minutes at a reaction ratio of 70%, to give a resin. The change in the softening point was determined, and the same procedures were further carried out with a next batch. The results are shown in Table IV-2.

TABLE VI-1

| Raw Material Monomers | Raw Material Monomer Composition A | Raw Material Monomer Composition B |
|---|---|---|
| Alcohol Component | | |
| BPA-PO[1] | 5,950 g (85) | 3,850 g (50) |
| BPA-EO[2] | 975 g (15) | 3,575 g (50) |
| Carboxylic Acid Component | | |
| Terephthalic Acid (TPA) | 1,926 g (58) | 2,739 g (75) |
| Trimellitic Acid (TMA) | 1,152 g (30) | — |
| Softening Point (° C.) | 140 | 95 |

Note)
The value in parentheses is expressed in a molar ratio, based on 100 mol of the total amount of the alcohol components.
[1] Polyoxypropylene(2.05)-2,2-bis(4-hydroxyphenyl)propane
[2] Polyoxyethylene(2.05)-2,2-bis(4-hydroxyphenyl)propane

TABLE VI-2

| | Catalyst[1] Type/Amount | Promoter[2] Type/Amount | Phosphorus-Containing Compound[3] Type/Amount | Timing of Addition | Reaction Ratio of Alcohol Component with TPA Upon Addition of Phosphorus-Containing Compound (%) | Time Period up to Point Where Reaction Ratio Reaches to 90% at First-Step Reaction (hr) | Time period of Vacuum Cross-Linking Reaction at Second-Step Reaction (min) | ΔTm | Reaction Time X of Next Batch (6.5 + X, hr) |
|---|---|---|---|---|---|---|---|---|---|
| Comp. Ex. VI-1 | A/0.5 | Pyrogallic Acid/0.05 | — | — | — | 3.0 | 50 | 4.7 | −1.5 |
| Comp. Ex. VI-2 | A/0.5 | Pyrogallic Acid/0.05 | a/0.2 | Upon Charging During First-Step Reaction | — | 8.5 | 150 | 1.2 | 0 |
| Ex. VI-1 | A/0.5 | Pyrogallic Acid/0.05 | a/0.2 | Before Charging TMA | 95 | 3.0 | 130 | 1.6 | 0 |
| Ex. VI-2 | A/0.5 | Pyrogallic Acid/0.05 | a/0.05 | Before Charging TMA | 95 | 3.0 | 100 | 2.8 | 0 |
| Ex. VI-3 | A/0.5 | Pyrogallic Acid/0.05 | a/1.5 | Before Charging TMA | 95 | 3.0 | 130 | 1.5 | +0.5 |
| Ex. VI-4 | A/0.5 | Pyrogallic Acid/0.05 | a/0.2 | 1 Hour Before Completion of Entire Reaction | 95 | 3.0 | 50 | 2.1 | 0 |
| Ex. VI-5 | A/0.5 | Pyrogallic Acid/0.05 | b/0.2 | Before Charging TMA | 95 | 3.0 | 110 | 2.0 | 0 |
| Ex. VI-6 | B/0.5 | Pyrogallic Acid/0.05 | a/0.2 | Before Charging TMA | 95 | 5.5 | 145 | 1.3 | 0 |
| Ex. VI-7 | A/0.5 | Pyrogallic Acid/0.05 | a/0.2 | In Process of First-Step Reaction | 70 | 6.5 | 125 | 1.7 | 0 |
| Ex. VI-8 | A/0.5 | Pyrogallic Acid/0.05 | a/0.2 | At Same Time as TMA | 95 | 3.0 | 105 | 2.0 | 0 |
| Comp. Ex. VI-3 | A/0.5 | TBC/0.05 | — | — | — | 6.0 | 90 | 3.5 | −0.5 |
| Ex. VI-9 | A/0.5 | TBC/0.05 | a/0.2 | Before Charging TMA | 95 | 6.0 | 135 | 1.5 | 0 |

Note)
The amount (parts by wt.) of the catalyst, the promoter, and the phosphorus-containing compound used is a weight ratio based on 100 parts by weight of the raw material monomers.
[1] Catalyst A: Tin(II) 2-ethylhexanoate Catalyst B: Titanium diisopropylate bis(triethanolaminate)
[2] TBC: t-butylcatechol
[3] Phosphorus-containing compound a: 1-Hydroxyethylidene-1,1-diphosphonic acid (commercially available from Solutia Japan Limited., DEQUEST 2010)
Phosphorus-containing compound b: Aminotri(methylene phosphonic acid) (commercially available from TOKYO KASEI KOGYO CO., LTD. reagent)

It can be seen from the above results that in Examples VI-1 to VI-9, the phosphorus-containing compound is added to the reaction system at a given point, whereby a progress of the reaction is properly controlled, and a resin with narrow distribution of a softening point is obtained, and also the influence of contamination of the resin on the next batch is small. On the other hand, in Comparative Examples VI-1 and VI-3 where the phosphorus-containing compound is not used, the reaction progresses even during the draw-out, and also the influence on the next batch is large, and in Comparative Example VI-2 where the phosphorus-containing compound has been added to the reaction system from the beginning of the reaction, the reaction time at the first-step reaction is long.

Example VI-10

Using raw material monomer composition B shown in Table VI-1, a 10-liter four-necked flask equipped with a nitrogen inlet tube, a dehydration tube, a stirrer, and a thermocouple was charged with the raw material monomers, and 0.5 parts by weight of catalyst A and 0.05 parts by weight of pyrogallol, based on 100 parts by weight of the raw material monomers. The ingredients in the flask were subjected to a polycondensation reaction at 235° C. under a nitrogen gas atmosphere until the reaction ratio reached to 90%. Thereafter, the reaction mixture was further reacted at 8 kPa for 1 hour (reaction ratio 95%). The pressure was then changed back to normal pressure, and the phosphorus-containing compound a was added to the reaction mixture in an amount of 0.2 parts by weight, based on 100 parts by weight of the raw material monomers, and the mixture was stirred for 1 hour. Thereafter, the resulting resin was drawn out. Here, catalyst A and phosphorus-containing compound a used are the same as that in Note under Table VI-2.

After the resin was drawn out, the same procedures as in Example VI-1 were carried out with a next batch. The reaction time was the same as the reaction time in the ordinary conditions (6.5 hrs).

Comparative Example VI-4

The same procedures as in Example VI-10 were carried out except that phosphorus-containing compound a was not used, to give a resin.

After the resin was drawn out, the same procedures as in Example VI-1 were carried out with a next batch. The reaction time was shorter than the reaction time in the ordinary conditions (6.5 hrs) by 1 hour.

[Change in Softening Point of Resin when Melt-Kneaded]

Each of the resins of Example VI-1 and Comparative Example VI-1 was melt-kneaded with a twin-screw extruder (set temperature of barrel: 200° C. (temperature of the resin during the melt-kneading: 210° C.)), and the softening points of the resin before and after the melt-kneading were determined. The results are shown in Table VI-3.

TABLE VI-3

| | Softening Point (° C.) | | |
|---|---|---|---|
| | Before Kneading | After Kneading | Difference |
| Ex. VI-1 | 142.5 | 149.6 | 7.1 |
| Comp. Ex. VI-1 | 140.7 | 142.1 | 1.4 |

It can be seen from the above results that in the resin of Example VI-1, the change in the softening point by the kneading is very small, as compared to that in the resin of Comparative Example VI-1.

The present invention being thus described, it will be obvious that the same may be varied in ways. Such variations are not to be regarded as a departure from the spirit and scope of the invention, and all such modifications as would be obvious to one skilled in the art are intended to be included within the scope of the following claims.

What is claimed is:

1. A polycondensation resin comprising a polyester unit having an ester bond (—COO—), a polyamide unit having an amide bond (—CONH—) or both produced by polycondensing raw material monomers using a promoter comprising a pyrogallol compound having a benzene ring of which three hydrogen atoms adjacent to each other are substituted by hydroxyl groups and at least one catalyst selected from the group consisting of a tin catalyst, a titanium catalyst, antimony trioxide, zinc acetate and germanium dioxide.

2. The polycondensation resin according to claim 1, wherein the pyrogallol compound is represented by the formula (I):

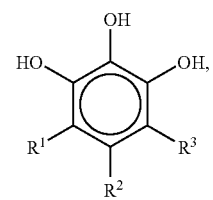

(I)

wherein each of $R^1$ to $R^3$ is independently a hydrogen atom or —COOR$^4$, wherein $R^4$ is a hydrogen atom or a hydrocarbon group having 1 to 12 carbon atoms.

3. The polycondensation resin according to claim 1, wherein said catalyst is a tin catalyst which is a tin(II) compound not having a Sn—C bond.

4. The polycondensation resin according to claim 1, wherein said catalyst is a titanium catalyst which is a titanium compound represented by the formula (A):

$$Ti(X)_n(Y)_m \qquad (A)$$

wherein X is a substituted amino group having 4 to 8 carbon atoms; Y is a substituted or unsubstituted, alkoxy group having 2 to 28 carbon atoms, a substituted or unsubstituted, alkenyloxy group having 2 to 28 carbon atoms, or a substituted or unsubstituted, acyloxy group having 2 to 28 carbon atoms; each of n and m is an integer of from 1 to 3, wherein the sum of n and m is 4.

5. The polycondensation resin according to claim 1, wherein said catalyst is a titanium catalyst which is a titanium compound represented by the formula (B):

$$Ti(Z)_4 \qquad (B)$$

wherein Z is a substituted or unsubstituted alkoxy group having 2 to 28 carbon atoms, a substituted or unsubstituted, alkenyloxy group having 2 to 28 carbon atoms, or a substituted or unsubstituted, acyloxy group having 2 to 28 carbon atoms.

6. The polycondensation resin according to claim 1, wherein said pyrogallol compound is at least one compound selected from the group consisting of pyrogallol, pyrogallic acid, a pyrogallic acid ester, 2,3,4-trihydroxybenzophenone, 2,2',3,4-tetrahydroxybenzophenone, epigallocatechin and epigallocatechin gallate.

7. The polycondensation resin according to claim 1, wherein said catalyst is a tin catalyst and is at least one selected from the group consisting of tin(II) oxalate, tin(II) acetate, tin(II) octanoate, tin(II) 2-ethylhexanoate, tin(II) laurate, tin(II) stearate, tin(II) oleate; octyloxy tin(II), lauroxy tin(II), stearoxy tin(II), oleyloxy tin(II); tin(II) oxide; tin(II) sulfate; tin(II) chloride and tin(II) bromide.

8. The polycondensation resin according to claim 1, wherein said catalyst is a titanium catalyst and is at least one selected from the group consisting of titanium diisopropylate bis(triethanolaminate), titanium diisopropylate bis(diethanolaminate), titanium dipentylate bis(triethanolaminate), titanium diethylate bis(triethanolaminate), titanium dihydroxyoctylate bis(triethanolaminate), titanium distearate bis(triethanolaminate), titanium triisopropylate triethanolaminate, titanium monopropylate tris(triethanolaminate), tetra-n-butyl titanate, tetrapropyl titanate, tetrastearyl titanate, tetramyristyl titanate, tetraoctyl titanate, dioctyl dihydroxyoctyl titanate and dimyristyl dioctyl titanate.

9. The polycondensation resin according to claim 1, wherein said resin comprises a polyester unit and said raw monomers comprise an alcohol component and a carboxylic acid component.

10. The polycondensation resin according to claim 9, wherein said alcohol component is an alkylene oxide adduct of bisphenol A represented by the formula (II):

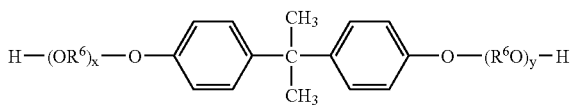

(II)

wherein $R^6O$ is an alkyleneoxy group, wherein $R^6$ is an alkylene group having 2 or 3 carbon atoms; and each of x and y is a positive number showing an average number of moles of alkylene oxide added, wherein the sum of x and y is from 1 to 16.

11. The polycondensation resin according to claim 10, wherein said alcohol component is at least one selected from the group consisting of ethylene glycol, 1,2-propanediol, 1,3-propanediol, 1,4-butanediol, 1,5-pentanediol, 1,6-hexanediol, 1,4-butenediol, 1,3-butanediol, neopentyl glycol and glycerol.

12. The polycondensation resin according to claim 10, wherein said carboxylic acid component is at least one selected from the group consisting of oxalic acid, malonic acid, maleic acid, fumaric acid, citraconic acid, itaconic acid, glutaconic acid, succinic acid, adipic acid, sebacic acid, azelaic acid, n-dodecylsuccinic acid, n-dodecenylsuccinic acid; phthalic acid, isophthalic acid, terephthalic acid; cyclohexanedicarboxylic acid, trimellitic acid, pyromellitic acid, acid anhydrides thereof, alkyl(1 to 3 carbon atoms) esters thereof and rosins modified with fumaric acid, maleic acid, acrylic acid.

13. The polycondensation resin according to claim 1, wherein said resin comprises a polyamide unit having an amide bond and said raw monomers comprise polyamines, aminocarboxylic acids and amino alcohols.

14. The polycondensation resin according to claim 1, wherein said promoter is used in an amount of 0.001 to 1.0 parts by weight based on 100 parts by weight of the raw material monomers used in the polycondensation reaction.

15. The polycondensation resin according to claim 1, wherein said catalyst is used in an amount of 0.01 to 2.0 parts by weight based on 100 parts by weight of the raw material monomers used in the polycondensation reaction.

16. The polycondensation resin according to claim 1, wherein a weight ratio of said promoter to said catalyst is from 0.01 to 0.5.

17. The polycondensation resin according to claim 4 wherein said pyrogallol compound is used in an amount of 0.001 to 1.0 part by weight, based on 100 parts by weight of the raw material monomers used in the polycondensation reaction.

18. A method for producing a polycondensation resin comprising a polyester unit having an ester bond (—COO—), a polyamide unit having an amide bond (—CONH—) or both by polycondensing raw material monomers using a promoter comprising a pyrogallol compound having a benzene ring of which three hydrogen atoms adjacent to each other are substituted by hydroxyl groups and at least one catalyst selected from the group consisting of a tin catalyst, a titanium catalyst, antimony trioxide, zinc acetate and germanium dioxide.

* * * * *